(12) United States Patent
Gross et al.

(10) Patent No.: US 6,186,982 B1
(45) Date of Patent: Feb. 13, 2001

(54) SUBCUTANEOUS DRUG DELIVERY DEVICE WITH IMPROVED FILLING SYSTEM

(75) Inventors: Joseph Gross, Dublin (IE); Zvi Nitzan, Petah-Tikva (IL); Izrail Tsals, Sundbury, MA (US); Mario Razonowich, Merkas Kafri Ezer (IL); Oz Cabiri, Makabim (IL); Haim Danon, Kiryat Ono (IL); Gilad Lavi, Holon (IL)

(73) Assignee: Elan Corporation, plc, Dublin (IE)

( * ) Notice: Under 35 U.S.C. 154(b), the term of this patent shall be extended for 0 days.

(21) Appl. No.: 09/072,875

(22) Filed: May 5, 1998

(51) Int. Cl.⁷ .................................................. A61M 37/00
(52) U.S. Cl. ...................... 604/132; 604/891.1; 604/141; 604/23; 604/67; 604/93.01; 604/48
(58) Field of Search .................................. 604/19, 48, 23, 604/65, 890.1, 891.1, 140, 141, 93, 173–174, 180, 131–133

(56) References Cited

U.S. PATENT DOCUMENTS

| | | | |
|---|---|---|---|
| 4,140,117 | 2/1979 | Buckles et al. | 128/213 R |
| 4,178,928 | 12/1979 | Tischlinger | 128/215 |
| 4,191,181 | 3/1980 | Franetzki et al. | 128/213 R |
| 4,196,732 | 4/1980 | Wardlaw | 128/218 |
| 4,258,713 | 3/1981 | Wardlaw | 128/218 |
| 4,640,445 | 2/1987 | Yamada | 222/386.5 |
| 4,684,367 | 8/1987 | Schaffer | 604/140 |
| 4,687,423 | 8/1987 | Maget et al. | 417/379 |
| 4,734,092 | 3/1988 | Millerd | 604/67 |
| 4,753,651 | 6/1988 | Eckenhoff | 424/449 |
| 4,758,226 | 7/1988 | Carre | 604/141 |
| 4,772,263 | 9/1988 | Dorman et al. | 604/132 |
| 4,886,499 | 12/1989 | Cirelli et al. | 604/131 |
| 4,902,278 | 2/1990 | Maget et al. | 604/132 |
| 5,024,656 | 6/1991 | Gasaway et al. | 604/70 |
| 5,024,661 | 6/1991 | Wender et al. | 604/110 |
| 5,045,064 | 9/1991 | Idriss | 604/132 |
| 5,098,385 | 3/1992 | Walsh | 604/131 |
| 5,135,507 | 8/1992 | Haber et al. | 604/187 |
| 5,152,753 | * 10/1992 | Laguette et al. | 604/153 |
| 5,242,406 | 9/1993 | Gross et al. | 604/132 |
| 5,266,013 | 11/1993 | Aubert et al. | 417/474 |
| 5,312,389 | 5/1994 | Theeuwes et al. | 604/892.1 |
| 5,324,258 | 6/1994 | Rohrbough | 604/86 |
| 5,391,151 | 2/1995 | Wilmot | 604/139 |
| 5,395,346 | 3/1995 | Maggioni | 604/195 |

(List continued on next page.)

FOREIGN PATENT DOCUMENTS

WO92/11879   7/1992   (WO) ............................ A61M/1/08

* cited by examiner

Primary Examiner—Angela D. Sykes
Assistant Examiner—Patricia M. Bianco
(74) Attorney, Agent, or Firm—Kathleen Maher Lynch

(57) ABSTRACT

A subcutaneous drug delivery device having a housing having an internal reservoir in communication with a drug delivery needle via a fluid path. An expandable chamber disposed adjacent to the reservoir forces drug from the reservoir to the needle when supplied with a gas. A flow regulating chamber, in communication with the fluid path, is capable of volumetric changes in response to temperature and/or pressure changes. An increase in the volume of the flow regulating chamber increases flow resistance to the needle and thereby counteracts the corresponding increase in delivery rate resulting from the expansion of the expandable chamber due to the same volumetric changes in response to temperature and/or pressure.

The device also includes an improved filling system that enables the reservoir within the device to be filled with drug from a source without regard to filling position and with a decreased risk of injury from needles. Moreover, the filling system provides an accurate measure of drug transferred into the device thus enabling patients to fill the devices and to ensure proper dosage upon delivery.

7 Claims, 29 Drawing Sheets

U.S. PATENT DOCUMENTS

| | | | |
|---|---|---|---|
| 5,395,501 | 3/1995 | Rohrbacker et al. | 204/265 |
| 5,527,288 | 6/1996 | Gross et al. | 604/140 |
| 5,545,143 | 8/1996 | Fischell | 604/180 |
| 5,562,624 | 10/1996 | Righi et al. | 604/110 |
| 5,613,951 | 3/1997 | Meyer et al. | 604/110 |
| 5,616,132 | 4/1997 | Newman | 604/185 |
| 5,624,401 | 4/1997 | Leijd | 604/110 |
| 5,637,092 | 6/1997 | Shaw | 604/110 |
| 5,693,018 * | 12/1997 | Kriesel et al. | 604/132 |
| 5,700,244 * | 12/1997 | Kriesel | 604/132 |
| 5,704,520 * | 1/1998 | Gross | 604/141 |
| 5,741,242 * | 4/1998 | Kriesel | 604/403 |
| 5,785,688 | 7/1998 | Joshi et al. | 604/141 |
| 5,814,020 * | 9/1998 | Gross | 604/41 |
| 5,840,071 * | 11/1998 | Kriesel et al. | 604/132 |
| 5,931,814 * | 8/1999 | Alex et al. | 604/131 |

SUBCUTANEOUS DRUG DELIVERY DEVICE WITH IMPROVED FILLING SYSTEM

TECHNICAL FIELD

This invention relates to a subcutaneous drug delivery device having an improved filling system.

BACKGROUND OF THE INVENTION

A wide range of subcutaneous drug delivery devices are known in which a drug is stored in an expandable-contractible reservoir. In such devices, the drug is delivered from the reservoir by forcing the reservoir to contract. (The term "subcutaneous" as used herein includes subcutaneous, intradermal and intravenous.)

Such devices can be filled in the factory or can be filled by the pharmacist, physician or patient immediately prior to use. In the former case it may be difficult to provide the required drug stability in the device since the drug will be stored in the reservoir for a shelf life of from several months to a number of years. In the latter case, it is difficult to ensure that the drug has completely filed the reservoir, i.e. that the reservoir and fluid path do not contain any air bubbles. In general, this requires priming the device by filling it in a certain orientation which ensures that the air bubbles are pushed ahead of the drug, such as with the filling inlet at the bottom and the delivery outlet at the top (to allow the bubbles of air to rise during filling).

A further problem associated with subcutaneous drug delivery devices is that in many cases gas generation is used to compress the reservoir. While it may be possible to ensure a constant or a controllably varying rate of gas generation (for example by passing a constant current through an electrolytic cell), this does not ensure a constant rate of drug delivery.

The amount of compression of the reservoir (and thus the rate of delivery of drug) depends on the amount by which the volume of the gas generation chamber expands. The behaviour of an ideal gas is governed by the equation $PV=nRT$, in which the volume of gas, V, is proportional to the number of moles of gas, n, and the temperature, T, and inversely proportional to the pressure, P.

An electrolytic cell working at constant current will generate a constant number of moles of gas per unit time. However, changes in the temperature of the gas and in the atmospheric pressure exerted on the gas will cause the volume to vary. Even if the temperature of the device remains constant, the fact that atmospheric pressure drops by approximately 3% for every increase in altitude of 300 m means that the delivery rate will vary substantially between a location at sea level and a higher altitude location (for example, Denver, Colo. is approximately 5 miles or 8 km above sea level, so atmospheric pressure will be approximately 15% lower on average than at sea level). Similarly, normal changes in atmospheric pressure due to the weather cause the delivery rate of this type of device to vary.

For devices which employ a needle to penetrate the skin there is a danger that after use the device may accidentally infect the patient or others if not properly disposed of. Our WO 95/13838 discloses an intradermal device of this type having a displaceable cover which is moved between a first position in which the needle is retracted before use and a second position in which the needle is exposed during use. Removal of the device from the skin causes the cover to return to the first position in which the needle is again retracted before disposal. However, this device does not include a locking mechanism in the assembly for locking the device prior to use to minimise accidental contact with the needle and/or accidental actuation of the device that may occur during shipping and/or storage.

When filling a drug delivery device, the conventional method is to use a syringe, which carries the risk of accidental injury. The present invention has as a further aim the improvement of safety when syringes are used. The present invention also aims to decrease the possibilities that the needle could become exposed by accident before or after use, for example, by a child playing with the device if not properly disposed of. Clearly given the risks associated with infectious diseases, particularly those carried by blood, any possibility of accidental infection must be minimised to the utmost and preferably eliminated entirely.

Our International Application No. PCT/IE 96/00059 discloses a medicament delivery device having a filling mechanism integral within the housing which receives a cylindrical cartridge (or "vial") sealed by a sliding stopper. When the cartridge is pushed into the filling mechanism, a hollow needle in the filling mechanism penetrates the stopper and establishes communication between the interior of the cartridge and the device's internal reservoir.

Continued movement of the cartridge into the filling mechanism causes the stopper to slide into the cartridge and act as a piston to pump the medicament from the cartridge into the reservoir. While this mechanism overcomes some of the disadvantages of using a syringe, it also makes the device bulkier.

Thus, there is a need to provide a subcutaneous drug delivery device having an improved filling mechanism which facilitates filling the device in an orientation-independent manner.

There is a further need to provide a filling system that is less bulky.

There is still a further need to provide a filling system that maintains the needles within the system in a recessed fashion so as to minimise the risk of injury associated with needles.

There is yet a further need to provide a device which operates at a substantially constant delivery rate independently of the ambient atmospheric pressure.

There is a further need to provide a drug delivery device in which the needle is retracted from the housing surface before and after use so as to minimise injury due to accidental contact with the needle.

There is yet a further need to provide a device having improved adhesion to the skin, i.e. for which there is less likelihood that the device will become detached during use.

SUMMARY OF THE INVENTION

The present invention overcomes these and other disadvantages associated with prior art drug delivery devices and filling systems. Stated generally, the present invention provides for a drug delivery device having a housing that has an internal reservoir and an expandable chamber disposed relative to the reservoir. The device also has a drug delivery needle extending from the housing for penetration of the skin of a subject. The needle has an outlet for drug delivery. The drug delivery device of the present invention further includes a fluid path defined between the delivery needle outlet and the reservoir and means for providing a gas at a controllable rate into the expandable chamber. The device also includes a flow regulating chamber, in communication with the fluid path, which is capable of volumetric changes in response to temperature and/or pressure changes.

By calibrating the degree of increase or decrease in flow resistance, it is possible to compensate for differences occurring in the rate of delivery which arise because of pressure- or temperature-induced differences in the volume of a given mass of gas in the expandable chamber. Thus, if the ambient atmospheric pressure drops, the gas in the expandable chamber will tend to expand and thereby force more drug from the reservoir. This will however be counteracted by the flow regulating chamber which will increase flow resistance along the fluid path and thereby counteract the increased flow rate arising from the effect of the tendency for the expandable chamber to expand.

Preferably, the expandable chamber causes contraction of the reservoir in use. Further, preferably, the flow regulating chamber alters the drug delivery rate by varying the flow resistance between the reservoir and the outlet. Preferably, the flow regulating chamber is associated with a blocking member which upon expansion of the flow regulating chamber moves within the fluid path so as to restrict the flow of drug.

Further, preferably, the blocking member comprises a formation provided on a displaceable member which at least partially bounds the flow regulating chamber, the formation being disposed adjacent to an inlet of a conduit forming part of the fluid path, such that restriction of the fluid path occurs when the blocking member is moved into the inlet of the conduit. By having a suitably shaped and sized formation relative to the inlet, it is possible to precisely vary the flow resistance of the conduit, and thereby precisely control the delivery rate notwithstanding changes in ambient temperature and/or pressure.

Suitably, the shape of the blocking member is adapted to cut off the fluid path completely with a predetermined degree of expansion of the flow regulating chamber. Alternatively, the formation can be shaped such that the fluid path is never entirely cut off.

In preferred embodiments of the invention, a displaceable cover is connected to the housing such that displacement of the housing relative to the cover when the cover has been applied to the skin of a subject causes the delivery needle to penetrate the skin of the subject. Such a displaceable cover is suitable for concealing the needle before and after application to the skin of a subject, which prevents injury and reduces the possibility of contamination of the needle.

In another aspect of the invention the expandable chamber is provided with a release valve operatively connected to the displaceable cover such that the movement of the housing relative to the cover controls the closing of the valve and thereby the sealing of the expandable chamber. This feature is not dependent on the existence of the flow regulating chamber.

The valve enables the device to be supplied with the displaceable member positioned such that the volume of the (empty) reservoir is minimised and that of the expandable chamber maximised. Thus, the reservoir can be of substantially zero volume initially, with no entrapped air volume. The device can then be primed or loaded by filling the reservoir, for example using a syringe- or cartridge-based filling mechanism. As the reservoir is filled, the displaceable member moves to expand the reservoir and thereby contract the expandable chamber. The valve allows the air or other gas in the expandable chamber to be exhausted into the atmosphere.

The device can then be applied to the skin of the user. When the device is applied the housing moves relative to the cover which is applied to the skin, not only does the needle penetrate the skin, but also (because the valve is operatively connected to the cover) the valve is closed to seal the expandable chamber. If the valve remained open then gas supplied into the expandable chamber would be free to escape and delivery would not be effected. While it would be possible for the user to close the valve manually, this would clearly leave open the possibility of error. Instead, by connecting the valve operatively to the cover, it is possible to ensure that the valve is always closed when the device is applied to the skin.

Preferably the valve comprises two components one of which is connected to the cover and the other of which is connected to the expandable chamber, such that relative movement of the housing towards the cover causes the valve to close.

The invention includes a displaceable cover that is displaceable relative to the housing between a first position in which the needle is concealed from the exterior of the device, and a second position in which the delivery needle protrudes from the device for penetration of the skin. A further aspect of the present invention comprises means for locking the device in the first position after a single reciprocation of the device from the first position to the second position and back to the first position.

The displaceable cover is an advantageous feature since it solves a problem unaddressed by prior art devices. Our prior art device has a locking mechanism to lock the housing in place after use and keep the needle concealed. However, there is no mechanism to prevent premature activation prior to intended use that may cause the needle to protrude accidentally thereby giving rise to injury. According to the present invention, however, the locking means engages automatically when the cover and housing are reciprocated relative to one another, i.e. the housing and cover are moved relative to one another to cause the needle to protrude when the device is applied to the skin. This relative movement is reversed when the device is removed thereby concealing the needle but also engaging the locking means to prevent the needle from being exposed again by accident.

In a preferred embodiment, the locking means comprises a mechanical latch which is brought into operation by the reciprocation. Further, it is preferred that the latch comprises a pair of elements mounted on the cover and the housing respectively. It is preferred that the elements be shaped such that they can have two relative configurations when the cover is in the first position relative to the housing. It is preferred the elements have a first movable configuration in which the elements are mutually movable, and a second locked configuration in which the elements are prevented from mutual movement. It is also preferred that the reciprocation of the cover and the housing causes the elements to pass from the first movable configuration, through an intermediate configuration when the cover is in the second position relative to the housing, and then to the second locked configuration, thereby preventing any further movement of the cover relative to the housing.

In preferred embodiments illustrated further below, one of the elements is provided with a recess which is adapted to receive a projection on the other of the elements, the recess and the projection being spaced apart from one another in the movable configuration, and being in engagement with one another in the locked configuration.

These embodiments are preferred because while they are mechanically simple and easy to make, their very simplicity provides fewer opportunities for malfunction.

In a preferred embodiment of the present invention, movement of the cover relative to the housing is initially prevented by a removable locking member. This feature helps to prevent accidental injury occurring because the needle is only exposed when the housing is moved relative to the cover, i.e. only after the user has specifically removed the removable locking member. The presence of the removable locking member also prevents the means for providing a gas from being actuated. This prevents the device from being exhausted by accidental switching on at an incorrect time. In a preferred embodiment of the present invention, the removable locking member comprises a laminar member inserted between the cover and the housing.

In a further aspect of the invention, the surface of the housing from which the needle extends or the surface of the displaceable cover, if present, is of a concave cross-section. When the device has been applied to the skin of a subject, removal of the device is resisted because the cover conforms more closely to the skin. In prior art devices, it has been found that retention on the skin of the user is problematic because of adhesive failure, for example. Using a concave surface causes the device to be retained more effectively by adhesive means.

With prior art devices the lower surface tends to be peeled away from the skin more easily as the edges of the device can be detached relatively easily. Where a concave lower surface is used the edges tend to remain in contact with the skin and removing the device is thus more difficult. In effect a shear force is required rather than a simple peeling, and this assists in preventing accidental removal. This feature is not dependent on the existence of the other aspects of the invention.

In a modified device according to the invention, the needle extends from the lower surface of the housing is replaced by a tube extending from the housing. The tube is adapted for carrying a drug delivery needle. Such a device is preferred for intravenous delivery of a drug as the needle carried on the end of the tube can be accurately located in a suitable vein. The needle may be integral with the tube or supplied separately.

In a further preferred feature of the present invention, the drug reservoir is separated from the expandable chamber by a diaphragm. The diaphragm exhibits bistable behaviour such that in one stable state the reservoir is full and in the other stable state the reservoir is empty. The diaphragm is shaped to minimise the energy required in the transition between the stable states. In a preferred embodiment of the present invention, the diaphragm is in the form of a body having a peripheral lip connected to a substantially flat central section by a flexible annular section. The flexible annular section assumes a substantially frusta-conical cross-section in one of the states and assuming an arcuate curved cross-section in the other state.

Preferably, the means for providing a gas comprises an electrical circuit in which any transistors are bipolar transistors having a gain of not less than 500, such that the circuit can be irradiated by ionising radiation without destroying the circuit.

This type of transistor has been found to be advantageous as it enables the device to be sterilised using gamma radiation with the electronic components intact. While a certain loss of performance results from the irradiation, the high gain transistor still has an adequate gain after irradiation to operate reliably. It is preferred that the current gain of the or each transistor is not less than 750. For example, a transistor having a rated current gain of 800 has been found to give an excellent performance after irradiation, despite the fact that irradiation lowers the current gain characteristics of the transistor by a factor of ten or more. The initial high gain compensates for the subsequent reduction arising from irradiation. The fact that the effects of irradiation can be predicted means that the performance after irradiation is reliable.

It is also preferred that the circuit further include a reference component across which a fixed potential drop is measurable. The reference component is essentially unchanged by the ionising radiation. If a reference voltage is used which is not affected by the irradiation process, then the operation of the other components in the circuit may be determined by this reference voltage. For example, while the current gain of a group of transistors may vary individually when a batch is irradiated, each such transistor can be used to make an identically functioning amplifier if the output current of the amplifier is matched against a given reference component.

Light emitting diodes (LEDs) have been found to be affected less than other standard components when irradiated by gamma radiation. Thus, the reference component of the preferred embodiment comprises a light-emitting diode. Gallium arsenide (GaAs) LEDs are virtually unaffected by gamma rays. Thus, it is preferred that the light emitting diode employs gallium arsenide as a semiconductor.

In a further aspect, the present invention provides for a subcutaneous drug delivery kit including a drug delivery device as described above. The device is provided with a filling mechanism associated with the reservoir. The filling mechanism includes means for receiving a filling adapter. The filling adapter includes a body which is adapted to accommodate a drug cartridge. The body has means for engaging the adapter-receiving means of the drug delivery device at one end thereof, means for receiving a cartridge at the other end thereof, and transfer means for transferring a liquid from a cartridge to the filling mechanism of the device as the cartridge is emptied. The adapter-receiving means and the corresponding engaging means provided on the adapter together constitute a releasable locking mechanism which holds the adapter in place on the device once engaged. The locking mechanism is disengaged by the cartridge when the cartridge is emptied within the adapter.

The kit according to the invention is advantageous because it eliminates the need for a bulky filling mechanism which accommodates the cartridge within the device, and instead employs an adapter which is releasable from the device so as to enable the filled device to be less bulky than prior art cartridge-based devices.

Furthermore, the locking mechanism employed is only disengaged when the cartridge has been completely emptied, i.e., the rubber stopper within the cartridge is pushed to the bottom. If the cartridge used is of a type which will empty when the stopper is pushed to the bottom, this feature ensures accurate loading of the reservoir, i.e. it is not possible to easily remove the device before the reservoir is filled with the correct dose of medicament.

Suitably, the transfer means comprises a hollow double-ended needle, one end of which is associated with the engaging means such that it communicates with the filling mechanism when the adapter is engaged with the device, and the other end of which is associated with the cartridge receiving means such that it communicates with the interior of a cartridge having a penetrable stopper when such a cartridge is received by the adapter.

Such a hollow double ended needle can be replaced by a pair of needles which are connected by a conduit, such as a moulded conduit running through the body of the adapter and having a needle mounted at either end such that it is functionally equivalent to a double ended needle. Preferably, both ends of the needle are disposed within the body of the adapter such that they are recessed from the exterior of the body when the adapter is disengaged from the device. This arrangement is preferable for safety reasons, as it allows the adapter to be disposed of without fear of accidental injury occurring from casual handling of the adapter.

In a preferred embodiment, the releasable locking mechanism comprises a pair of locking members provided on the adapter receiving means and the corresponding engaging means, respectively. One of the locking members is movable between a locking position and a disengaging position. The movable locking member is disposed relative to the body such that, in use, when a cartridge is emptied within the body, the movable locking member is moved from the locking position to the disengaging position under the action of the cartridge.

Where a substantially cylindrical cartridge is employed, the body can receive the cartridge within a passage having a diameter sufficient to completely accommodate the cartridge. However, the end of the passage is of slightly narrower diameter on account of a projection provided on the movable locking member. Thus, when the cartridge completely emptied by pushing the stopper to the bottom, it contacts the movable locking member and pushes it out of the way, thereby disengaging the locking mechanism.

Suitably, the movable locking member is resiliently biased towards the locking position. Preferably, the movable locking member is a latch which automatically locks the adapter and device to one another when engaged together. It is preferred that the cartridge is emptied by moving the penetrable stopper against the adapter.

The present invention further provides a subcutaneous drug delivery kit including a device according to any preceding claim further comprising a filling mechanism associated with the reservoir, the filling mechanism comprising means for receiving a filling adapter as defined herein and a filling adapter. The filling adapter has a body adapted to receive a syringe. The body has means for engagement with the adapter-receiving means of the device at one end thereof, syringe-receiving means at the other end thereof and transfer means for transferring a liquid from the syringe to the filling mechanism of the device as the syringe is emptied. The transfer means includes a conduit associated with the syringe receiving means, the conduit leads to a needle which is associated with the engagement means and is disposed within the body of the filling adapter.

It is preferred that the needle disposed within the body of the filling adapter is recessed from the exterior of the body when the adapter is disengaged from the device. It is also preferred that the adapter receive the syringe without a needle. Since the needle on the adapter is recessed from the exterior of the adapter body and the syringe has no needle when filling, a conventional syringe (minus needle) can be used to fill the device without any risk of accidental injury.

A further aspect of the present invention provides a method of filling a drug delivery device. The method includes providing a drug delivery device having a drug reservoir. The reservoir is associated with a filling mechanism having filling adapter receiving means. The method further includes providing a filling adapter having a first end for engagement with the adapter receiving means, and a second end for receiving a syringe and causing the filling adapter receiving means to receive the filling adapter. The method further includes causing the second end of the filling adapter to receive a syringe having liquid stored therein and a needle, and providing a conduit for communication between the liquid stored within the syringe and the first end of the filling adapter. The method of filling further includes emptying the syringe and concurrently transferring the liquid from the syringe to the device via the conduit. In yet further aspects, the invention provides a filling adapter as defined above and a diaphragm as defined above.

Thus, it is an object of the present invention to provide a subcutaneous drug delivery device having an improved filling mechanism which facilitates filling the device in an orientation-independent manner.

It is a further object of the present invention to provide a filling system that is less bulky.

It is still a further object of the present invention to provide a filling system that maintains the needles within the system in a recessed fashion so as to minimise the risk of injury associated with needles.

It is yet a further object of the present invention to provide a device which operates at a substantially constant delivery rate independently of the ambient atmospheric pressure.

It is even yet a further object of the present invention to provide a drug delivery device in which the needle is retracted from the housing surface before and after use so as to minimise injury due to accidental contact with the needle.

It is yet a further object of the present invention to provide a device having improved adhesion to the skin, i.e. for which there is less likelihood that the device will become detached during use.

Other objects, features and advantages of the present invention will be apparent upon reading the following specification taken in conjunction with the drawings and appended claims.

BRIEF DESCRIPTION OF THE DRAWINGS

The invention will be further illustrated by the following description of embodiments thereof, given by way of example only with reference to the accompanying drawings, in which.

DETAILED DESCRIPTION OF THE INVENTION

Figure 1:
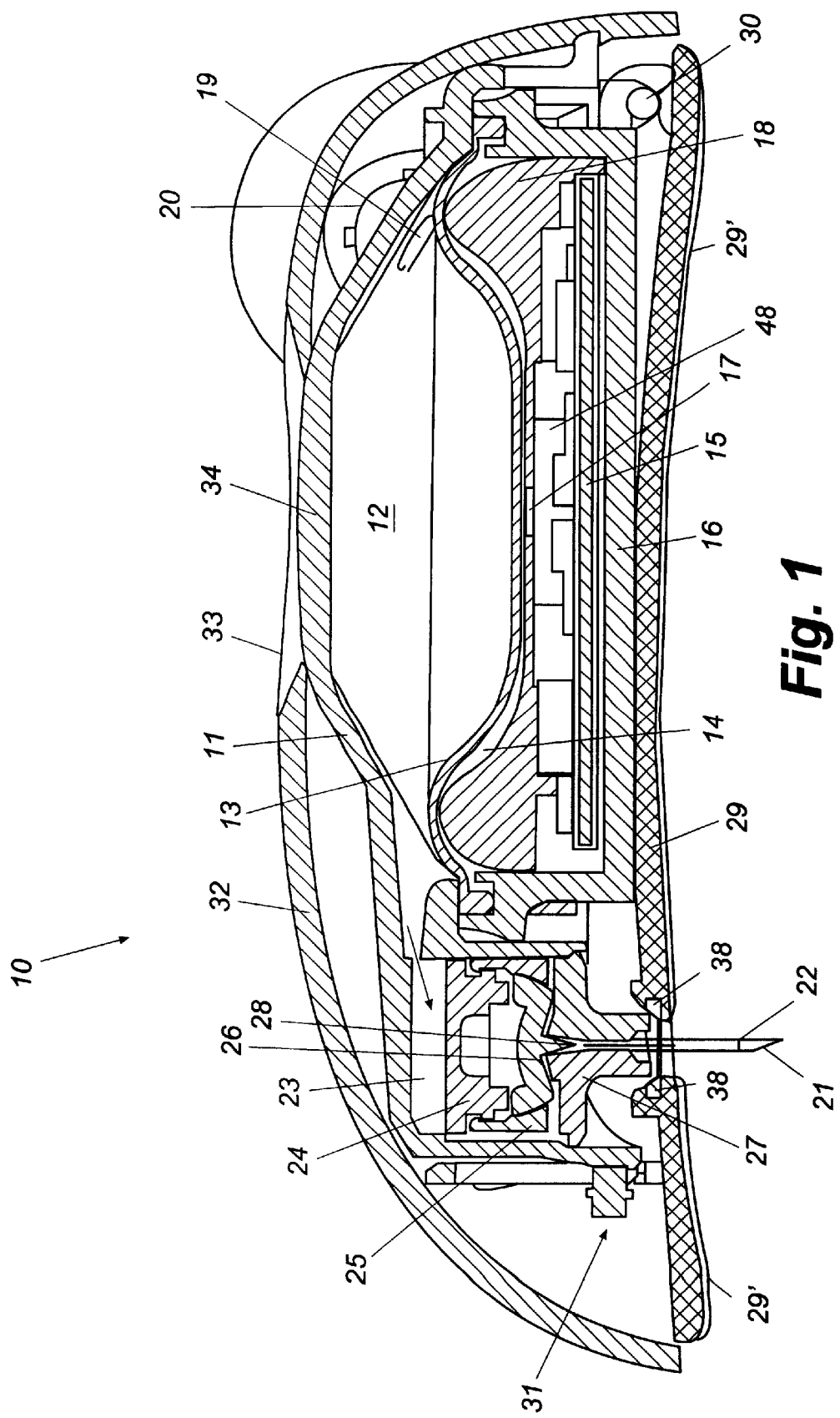
FIG. 1 is a sectional side view of a first embodiment of drug delivery device according to the present invention.

Referring now in more detail to the drawings, in which like numerals refer to like parts throughout the several view, FIG. 1 indicates a subcutaneous drug delivery device 10 according to the invention. A housing 11 defines a reservoir 12 which is partially bounded by an elastomeric diaphragm 13 which allows the reservoir to expand and contract. The diaphragm 13 also bounds an expandable chamber 14 such that expansion of the expandable chamber causes the reservoir 12 to contract and vice versa. In FIG. 1, the reservoir 12 is at full volume and contains a drug, while the expandable chamber 14 is at minimum volume.

A circuit board 15 having an electrolytic cell 48 mounted thereon (explained in greater detail below) is mounted in the lower part 16 of the housing 11. In use, the electrolytic cell 48 feeds a gas into the expandable chamber 14 via an aperture 17 in a supporting member 18.

The reservoir 12 is provided with an inlet 19 which is in communication with a filling mechanism 20 (explained in greater detail below). A delivery needle 21 provided with an outlet 22 is in communication with the reservoir 12 via a fluid path 23 which is indicated by arrows. The fluid path 23 passes around an air-filled flow-regulating chamber 35 which comprises a top member 24, annular member 25 and flow diaphragm 26. The fluid path 23 also passes via a needle holder 27 to the needle 21. The inlet 37 to the needle 21 is partially restricted by a projection 28 on the flow diaphragm 26, such that any upward movement of the projection 28 reduces resistance to flow and any downward movement of the projection increases flow resistance.

Figure 2:
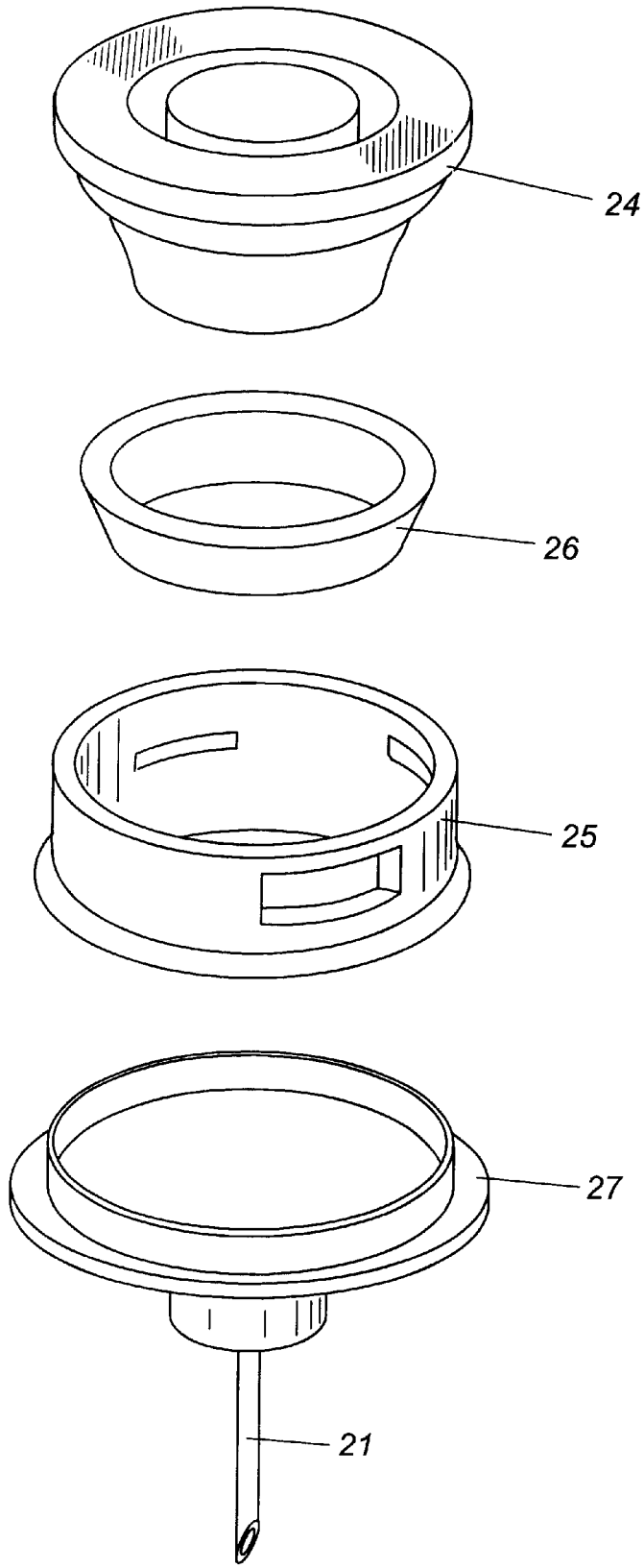
FIG. 2 is an exploded perspective view of the flow regulating chamber and needle assembly of the first embodiment of the device of FIG. 1.

Referring additionally to FIG. 2, the flow regulating chamber 35 can be seen in exploded view. Annular member 25 receives the flow diaphragm 26, and top member 24 and the three components fit together to form an airtight chamber 36 which is positioned above the needle holder 27. The inlet 37 in the needle holder 27 leading to the needle 21 can be clearly seen on the top surface of the needle holder. Projection of the flow diaphragm as shown in FIG. 37 extends into the inlet.

Figure 4:
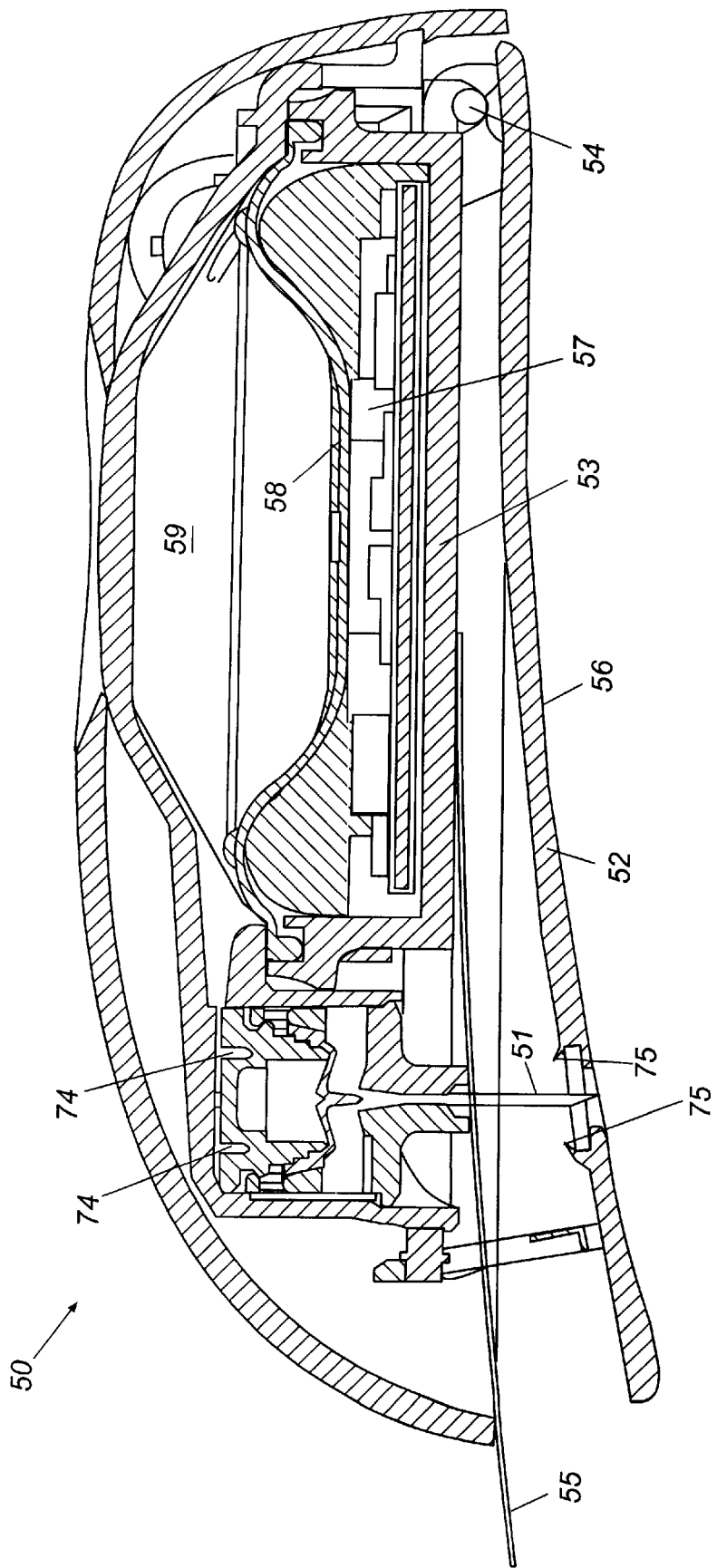
FIGS. 4–6 are sectional side views of a second embodiment of drug delivery device according to the invention, shown before, during and after use, respectively.

Further features of device 10 which can be seen in FIG. 1 are a displaceable cover 29 attached to the housing 11 by a hinge 30. The movement of the displaceable cover 29 between the position shown in FIG. 1 (wherein the needle 21 protrudes through the displaceable cover) and a position in which the needle 21 is substantially concealed by the displaceable cover 29 (as shown in FIG. 4), is controlled by a locking mechanism indicated generally at 31 and explained in greater detail below.

In use, the displaceable cover 29 is affixed to the skin using an adhesive coating 29' provided on the surface thereof distal from the housing ("the underside"). The displaceable cover 29 has a concave shape when viewed from the underside. This shape is advantageous because if a flat or convex surface is provided, the edges of the cover 29 will be more easily peeled away from the skin by accident, i.e. the use of a convex surface is less likely to have protruding edges, and the force required to peel the device away is a shear force rather than a simple peeling force.

The housing 11 is covered by a protective top cover 32 which can provide a more aesthetically pleasing appearance to the device, as well as one which is ergonomically more advantageous for the user. An aperture in protective top cover 32, indicated at 33, allows a transparent portion 34 of the housing 11 to be seen, thereby allowing the user to visually check the reservoir to see whether drug is present. The protective top cover 32 also protects the housing 11 and its component parts if the device 10 is mishandled or dropped The flow regulating chamber 35 is shown in greater detail in FIG. 3 and comprises the top member 24, the annular member 25, and the flow diaphragm 26, as explained above. The construction ensures that the airtight space 36 exists in the interior of the chamber 35. A fluid path between the reservoir and the needle (FIG. 1) is shown with heavy arrows. As can be seen, projection 28 on the flow diaphragm 26 extends into the inlet 37 in the needle holder 27 leading to the needle 21. The fluid has to push up on the flow diaphragm 26 in order to reach the needle 21. Little force is required to do this, as the air in the chamber 35 is compressible.

However, if the ambient atmospheric pressure drops, for example due to an increase in altitude, the fixed mass of air in the chamber 35 tends to expand (since for ideal gases at fixed temperature the product of pressure and volume is a constant). This makes it more difficult for fluid to flow past the flow diaphragm 26 into needle holder 27 and would thus tend to cause a decrease in the rate of delivery of drug.

The fact that the drug is being driven by a gas-filled expandable chamber 14, however, means that the expandable chamber tends also to increase in volume due to this increase in altitude, and the effect of an increase in expandable chamber volume is to speed up the rate of delivery.

Therefore, by calibrating the flow regulating chamber 35 correctly, barometric changes which would otherwise tend to increase or decrease the rate of delivery of drug are counteracted by the corresponding increase or decrease in the amount of flow resistance exerted by the flow regulating chamber, thereby allowing a constant delivery rate to be maintained. It will be appreciated that changes in temperature which would cause the gas in the expandable chamber to expand or contract are also counteracted in the same way.

Figure 3:
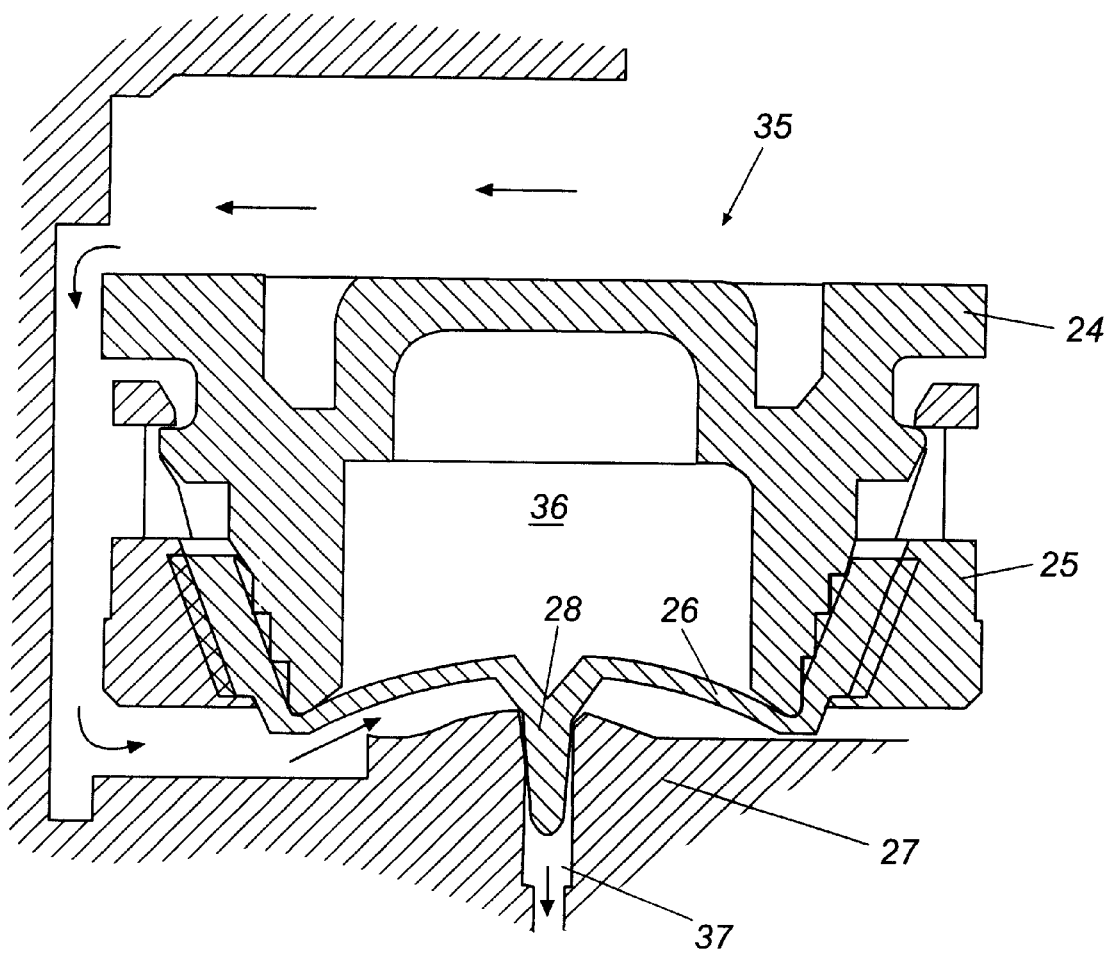
FIG. 3 is an enlarged sectional side view of the flow regulating chamber and needle assembly of the first embodiment of the device of FIG. 1.

A further feature of the device of FIGS. 1–3 is an o-ring 38 located on displaceable cover 29 (see FIG. 1). The o-ring 38 forms a seal with needle holder 27 and thereby assists in protecting the puncture point of the needle 21 into the skin of the user from contact with soap, water, perspiration or other contaminates. If water or other liquid contacts the needle 21, the needle 21 may act as a switch and allow water to be drawn into the puncture. However, adhesive 29' on the displaceable cover 29 prevents water from reaching the needle 21 via the underside of the cover, and the o-ring 38 prevents water from reaching the needle via the upper side of displaceable cover.

Top member 24, annular member 25, flow diaphragm 26 and needle holder 27 and all other parts in the fluid pathway are preferably made of a polycarbon material. Polycarbon materials are essentially inert and will not react with the liquid drug. Moreover, the polycarbon material withstands gamma radiation without degradation of any properties.

Figure 5:
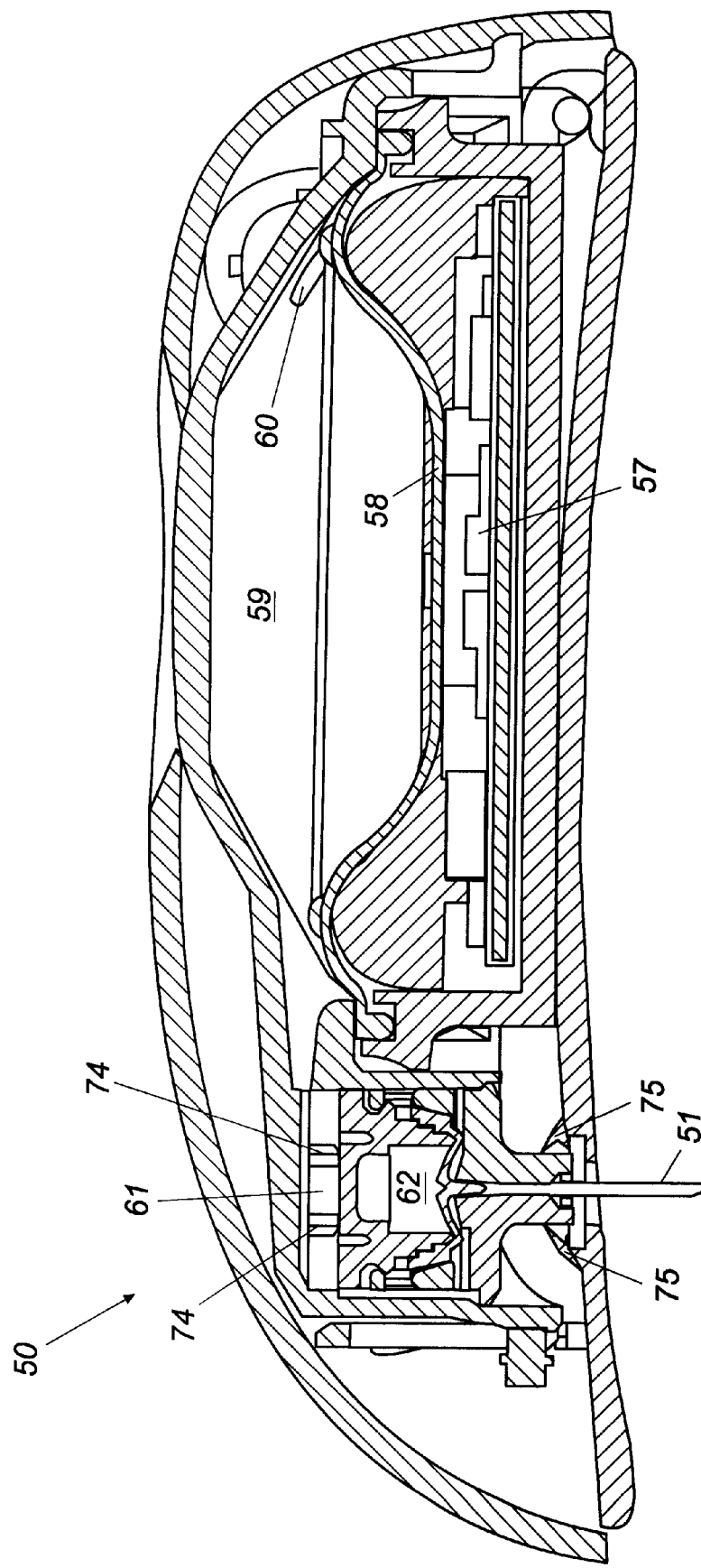
Figure 6:
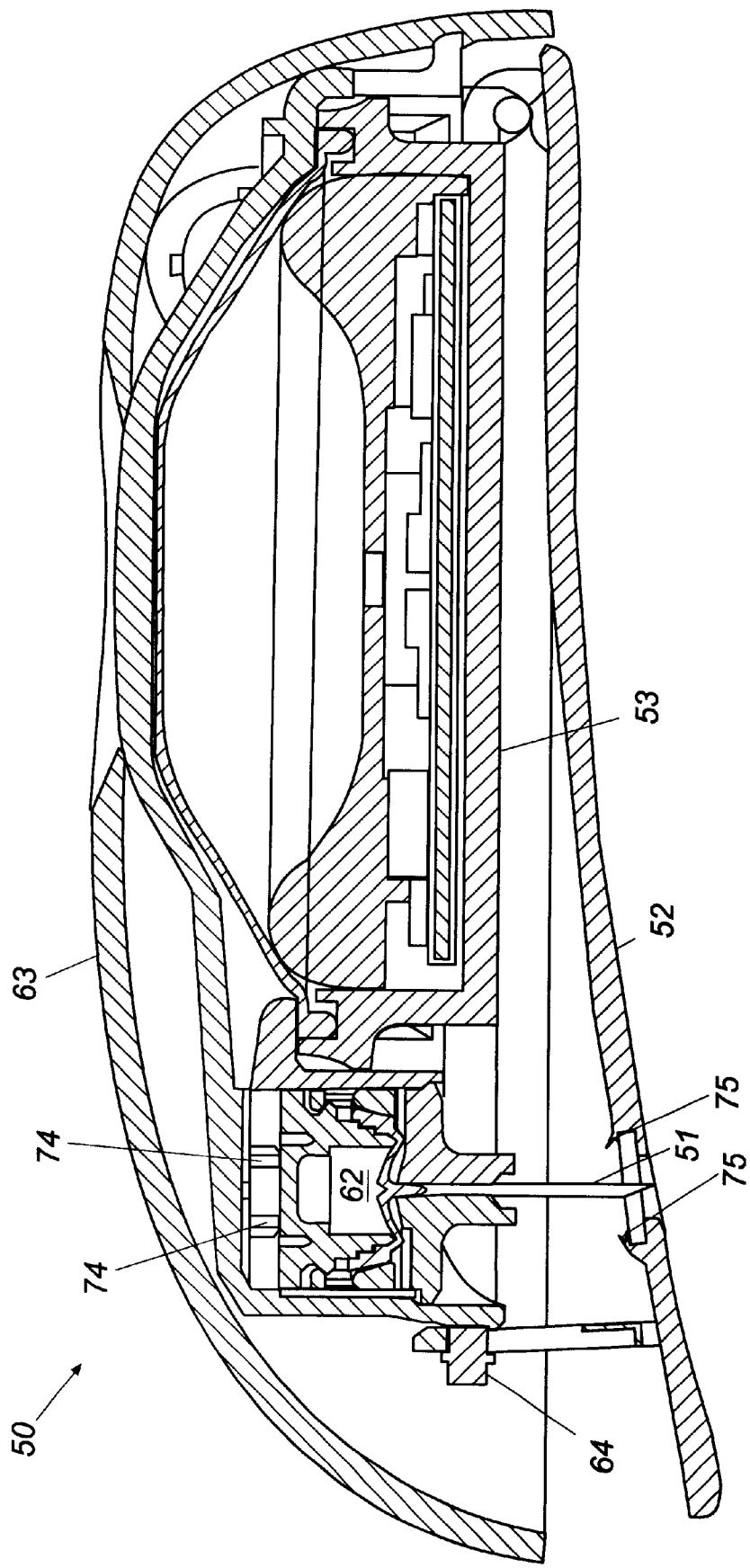

FIGS. 4, 5 and 6 show a device similar to that of FIG. 1 before, during and after use, respectively. The device, indicated generally at 50, differs slightly from the FIG. 1 device and accordingly different reference numerals are used in relative to FIG. 1. The device 50 is shown in FIG. 4 with the needle 51 concealed by the displaceable cover 52 because the displaceable cover 52 is displaced relative to the housing 53 about the hinge 54. A removable tab 55 prevents the displaceable cover 52 from being moved towards housing 53, as will be described further below. The underside 56 of the displaceable cover 52 is coated with a contact adhesive 56, and during storage, the adhesive is protected by a release liner (not shown).

When the release liner is removed, the adhesive-coated underside 56 is pressed against the skin to ensure good adhesion (the concave surface assists in obtaining good adhesion) and the tab 55 is removed. The housing 53 is then pushed towards the skin and the needle 51 penetrates the skin as the displaceable cover 52 and housing 53 move together about hinge 54, leading to the configuration shown in FIG. 5.

A start button (not shown) is pressed to activate a gas generating electrolytic cell 57 (see FIG. 5). As gas is generated, a diaphragm 58 is pushed upwards to drive a liquid drug from the reservoir 59 (which was filled before use via inlet 60) and thereby force the drug through a fluid path 61 around the flow regulating chamber 62 (as explained above in relation to FIGS. 1–3) and to the patient via the delivery needle 51.

When delivery has been completed, the diaphragm 58 will have moved up such that the space occupied by the reservoir 59 at the beginning of delivery (see FIGS. 4 and 5) is now occupied by the expandable chamber 60 (see FIG. 6), since the expansion of the expandable chamber causes contraction of the reservoir.

The device 50 is removed from the skin by pulling upwards on the upper protective cover 63 (FIG. 6). This causes the needle 51 to be retracted behind the displaceable cover 52 once again because the adhesive force holding the displaceable cover 52 against the skin is greater than the force exerted by the locking mechanism 64 (explained in greater detail below). Once the needle 51 is retracted in this way, the locking mechanism 64 holds the displaceable cover 52 permanently in the position shown in FIG. 6, i.e. away from the housing 53 with the needle 51 concealed.

Figure 7:
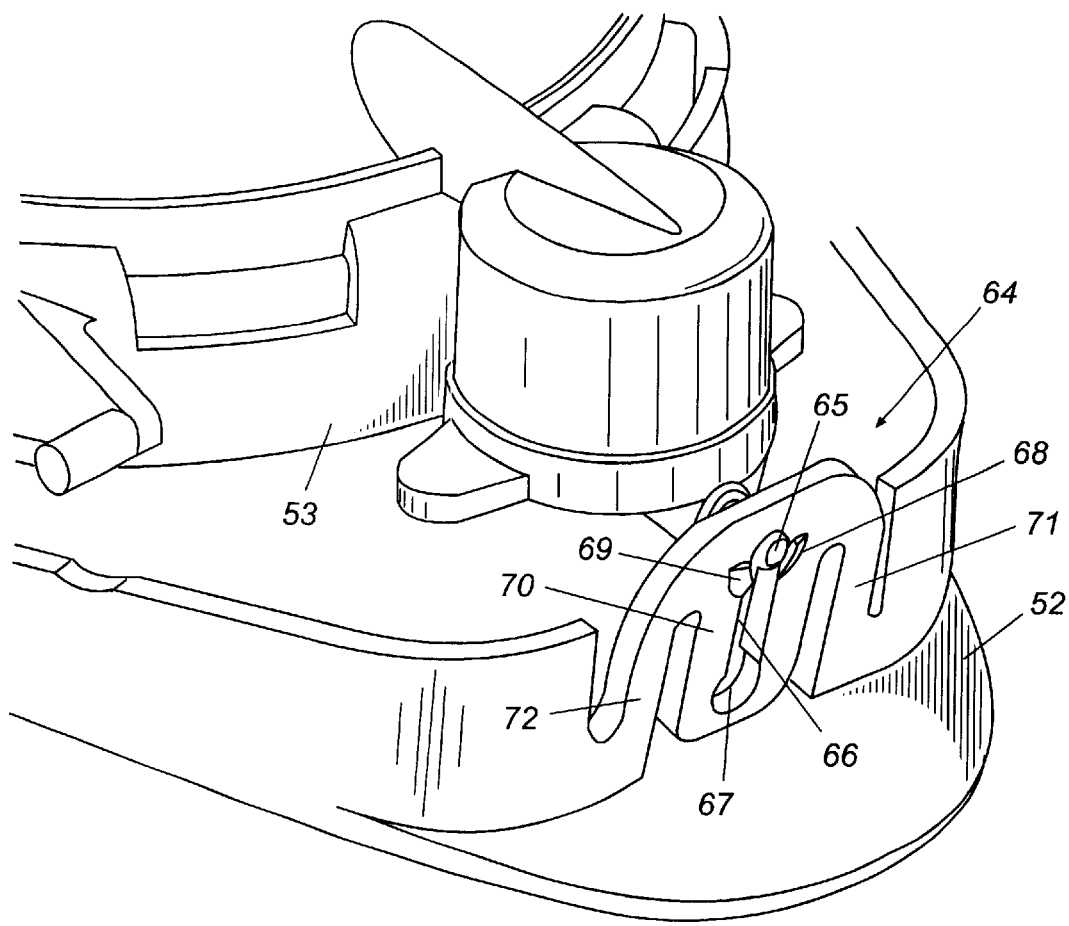
FIGS. 7–9 are enlarged perspective views of the locking mechanism of the device of FIGS. 4–6, shown before, during and after use, respectively.

FIG. 7 shows locking mechanism 64 in greater detail, with the protective top cover 63 removed for illustrative purposes. The locking mechanism 64 is illustrated before use, i.e. when the displaceable cover is positioned as shown in FIG. 4. In other words, there is a gap between the housing 53 and the displaceable cover 52, and the needle 51 (FIG. 4) is recessed in this gap and thereby concealed by the displaceable cover 52. A projection 65 mounted on the front of housing 53 is positioned at the upper end of a slot 66. The slot 66 has an enlarged portion 67 at the lower end and is provided with wedge projections 68,69 at the exterior surface of the upper portion thereof. The slot 66 is formed in a member 70 which is attached to displaceable cover 52 by connecting arms 72 which allow a slight degree of flexibility. A widened rib (not shown in FIG. 7) is provided on the projection 65, and the width of this rib is greater than that of the upper portion of the slot 66. The member 70 is biased slightly against this rib.

Figure 8:
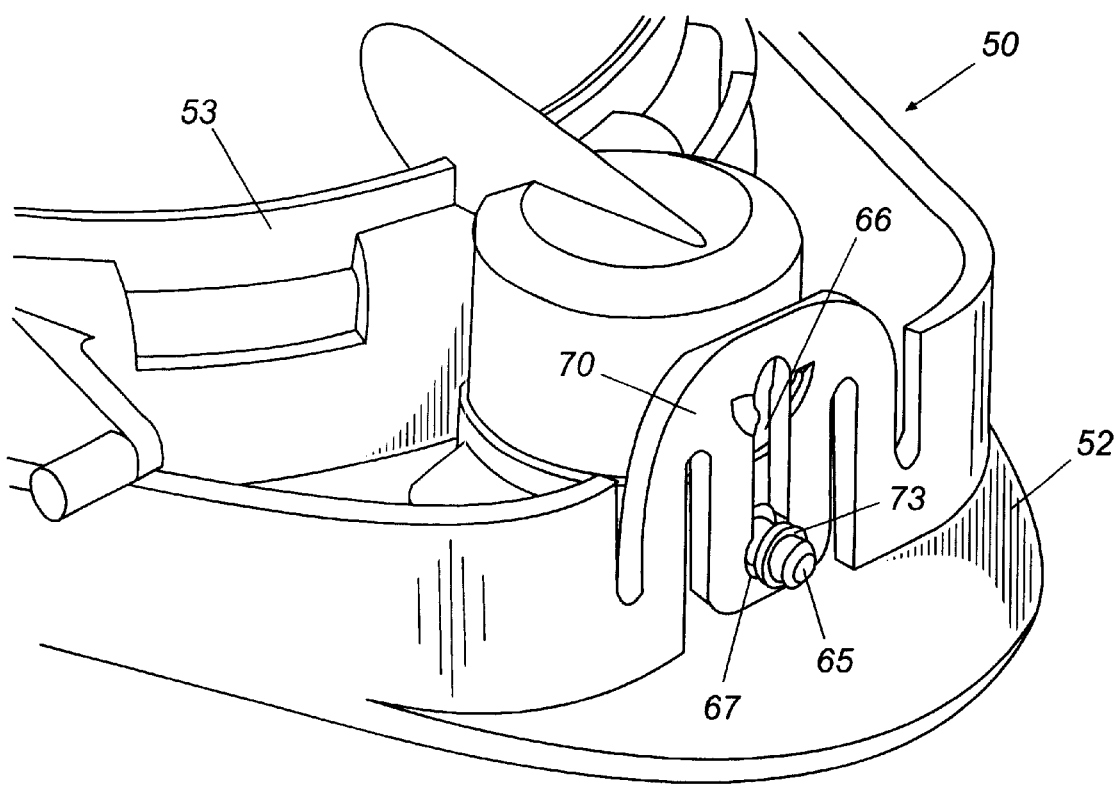

The removable tab 55 (see FIG. 4) is positioned so as to engage wings 71 and prevent them from moving towards the cover 52. This effectively prevents the entire housing 53 from being moved towards the cover 52 and prevents the device from being activated prematurely. When the tab 55 is removed, as shown in FIG. 7, the displaceable cover 52 can be snapped towards the housing 53 by pressing down on the housing. This results in the locking mechanism adopting the configuration shown in FIG. 8, wherein the projection 65 has moved to the lower end of the slot 66, allowing a lipped member 73 to pass through the enlarged portion 67 at the lower end of slot 66. This allows a member 70, which was biased in the direction of projection 65, to relax. The sides of the lipped member 73 rest against the member 70

Figure 9:
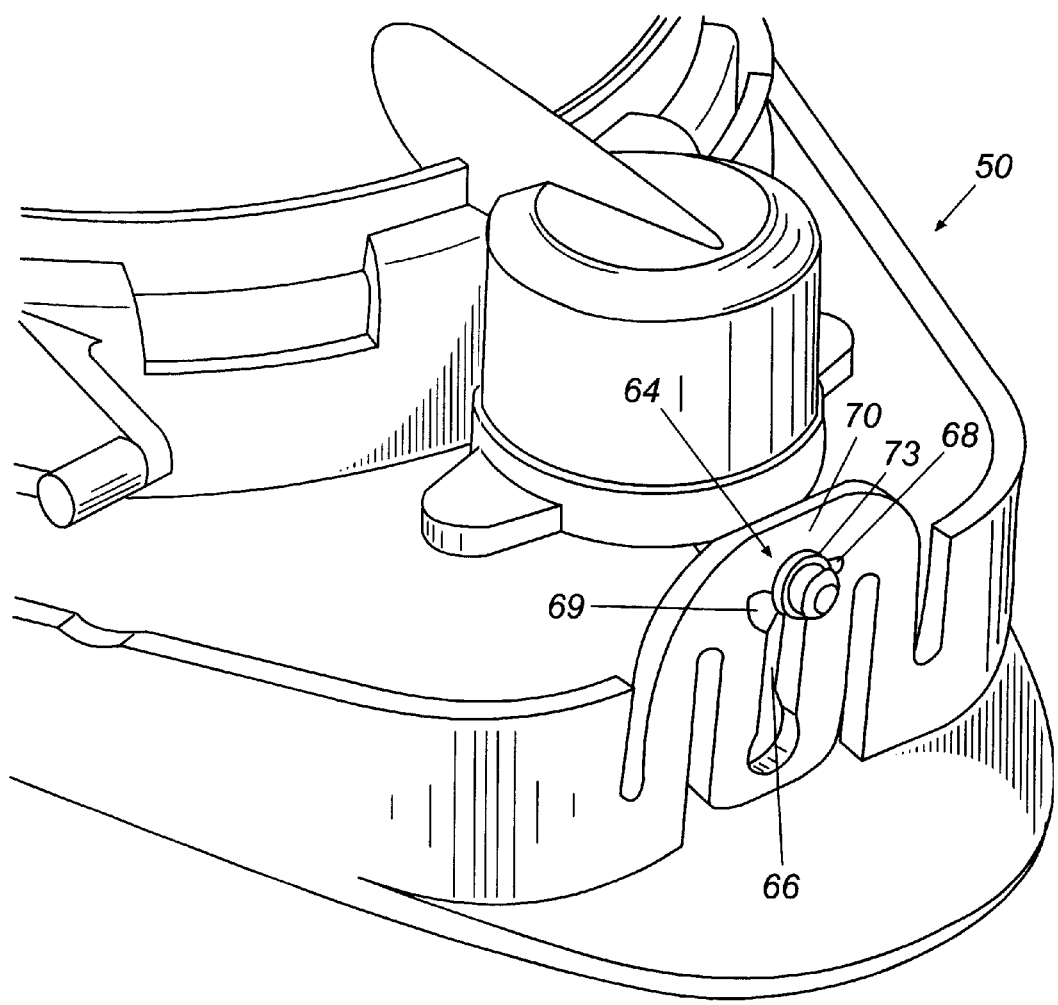

When delivery is complete and the housing 53 is lifted away from the displaceable cover 52, this disengages the lips of the lipped member 73 from resting against member 70 and again moves the projection 65 to the upper end of the slot 66. However, the lipped member 73 passes over the wedge projections 68,69, as shown in FIG. 9. When this happens, the wedge projections 68,69 catch the lipped member 73 and prevent it from moving back down. This effectively locks the locking mechanism 64 permanently in the configuration shown in FIG. 9, thereby concealing the needle 51 permanently from view and making the device 50 safe for disposal.

An additional feature of the device of FIGS. 4–8 relative to that of FIG. 1 can be seen with reference to FIGS. 4–6. A pair of projections 74 grip the flow regulating chamber 62 before use to block the path between the reservoir 59 and the needle 51 before use (FIG. 4). When gas generation begins, the pressure of liquid in the reservoir 59 forces the flow regulating chamber 62 downwards relative to the projections 74. The projections 74 are resilient and move together when the flow regulating chamber 62 moves downwards. In this position the projections 74 hold flow regulating chamber 62 in a fixed position both during delivery (FIG. 5), and when the device is removed from the skin (FIG. 6). Thus, after delivery, accidental leakage of medicament from the needle 51 (e.g. due to gravity) is prevented by the fixed position of the flow regulating chamber 62.

A further feature of the embodiment of FIGS. 4–6 is an annular elastomeric inwardly extending lip 75 which seals the skin at the point of entry of the needle 51 in the same manner as the o-ring 38 in the FIG. 1 embodiment. This feature reduces the danger of infection due to wicking by the needle of unwanted substances into the skin.

Four alternative embodiments of different locking mechanisms according to the invention are shown in FIGS. 10A–10D, 11A–11D, 12A–12D, and 13A–13E. In each case the mechanism is shown schematically in "pre-use" (A), "in-use" (B) and "post-use" (C) configurations as well as in one or two perspective views (D/E). The mechanism can in each case be moved from position A to position B and from position B to position C with little difficulty (although generally some resistance is present to prevent spontaneous or accidental movement), but once in position C, the mechanism is effectively locked permanently and is no longer capable of operation.

Figure 10A:
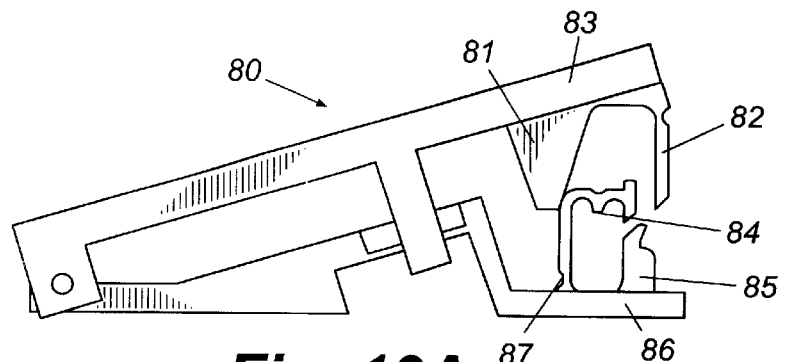
FIGS. 10A, 10B and 10C are schematic elevations of a first alternative embodiment of a locking mechanism, shown before, during and after use, respectively.

The first alternative embodiment of a locking mechanism comprises a resilient arm and related assembly and is shown in FIGS. 10A–10D. In FIG. 10A the locking mechanism is indicated generally at 80 and comprises a biasing member 81 and a resilient strut 82 mounted on a housing 83, and the resilient arm 84 and a post 85 mounted on a displaceable cover 86.

The resilient arm 84 is flexibly hinged at the base thereof 87. When the housing 83 is pushed towards the displaceable cover 86, the biasing member 81 pushes the resilient arm 84 against the post 85. The resilient arm 84 and post 85 are mutually shaped to allow the arm 84 to pass over the top of the post 85, where it latches (see FIG. 10B) and is prevented from returning to the position shown in FIG. 10A.

Figure 10B:
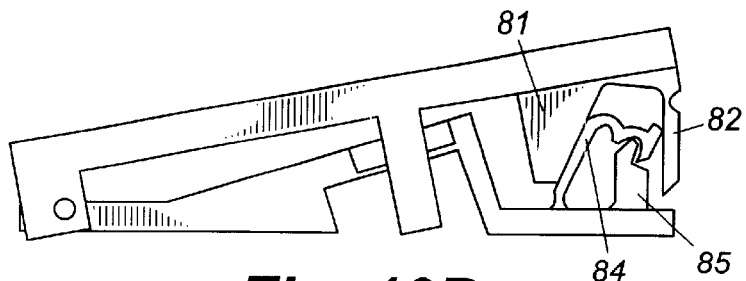

In passing over the top of the post 85, the arm 84 acts against the resilient strut 82, momentarily bending the strut 82 away from the biasing member 81. Although when the arm 84 has passed fully over the top of the post 85 the strut 82 has returned to its relaxed (straight) position (FIG. 10B).

When (after use) the housing 83 is pulled away from the displaceable cover 86, this causes the strut 82 to again be bent away from biasing member 81 (because arm 84 which is now locked in place by post 85 impedes the path of strut 82). However, when the end 88 of strut 82 has cleared the arm 84, it springs back into position, past a projection 89 on arm 84 (see FIG. 10C). In fact, strut 82 latches behind projection 89, preventing the strut from moving back to the position shown in FIG. 10B, and thereby permanently locking the mechanism 80 in the FIG. 10C configuration.

Figure 10C:
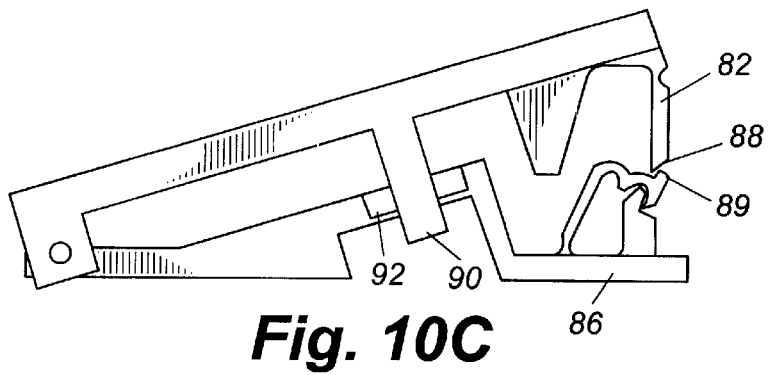
Figure 10D:
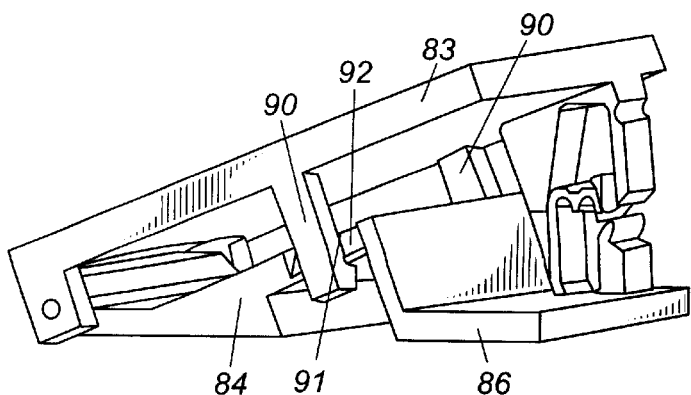
FIG. 10D is a perspective view of the locking mechanism as shown in FIG. 10A.

The perspective view in FIG. 10D shows the mechanism in the position illustrated in FIG. 10A. An additional feature visible in FIG. 10D is a snap mechanism comprising an arm 90 depending from either side of the housing 83. A raised protuberance 91 on the inner surface of each arm 90 acts against a sloped surface 92 on the displaceable cover 86 to provide resistance to movement. The effect of the snap mechanism is to add further resistance to any unintended relative movement between the housing 83 and the displaceable cover 86. A further effect is that the movement of the housing 83 relative to the cover 86 between the configurations of FIGS. 10A and 10B, and the configurations of FIGS. 10B and 10C, is extremely rapid, causing the penetration of the needle into the skin and the removal of the needle from the skin to be quick and painless.

Figure 11A:
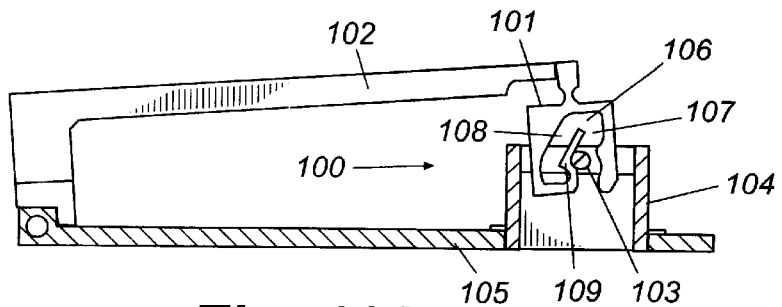
FIGS. 11A, 11B and 11C are schematic elevations of a second alternative embodiment of a locking mechanism, shown before, during and after use, respectively.

The second alternative embodiment of a locking mechanism of the present invention comprises an inverted V-shaped assembly and is shown in FIGS. 11A–11D. In FIG. 11A the locking mechanism is indicated generally at 100 and comprises a member 101 resiliently mounted on a housing 102, and a pin 103 supported in a frame 104 mounted on a displaceable cover 105. The member 101 has an inverted V-shape slot 106 therein. The slot 106 has an outer slot portion 107 connected at the upper end thereof to an inner slot portion 108, and a dividing member 109 between the outer and inner slot portions 107, 108 below the upper ends.

In moving from the "pre-use" position to the "in-use" position, the (fixed) pin 103 moves up the outer slot 107, acting against the dividing member 109 until it springs past the dividing member 109 at the top of the outer slot. In the position shown in FIG. 11B, the pin 103 is located above the top of the inner slot 108.

Figure 11B:
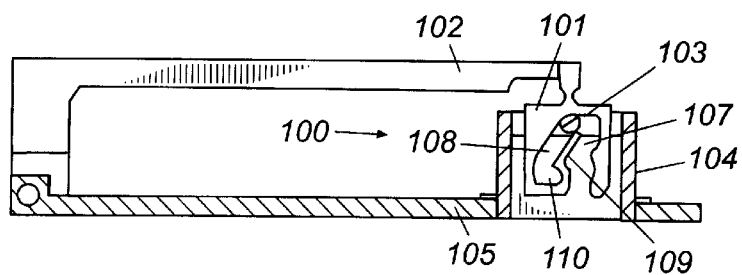
Figure 11C:
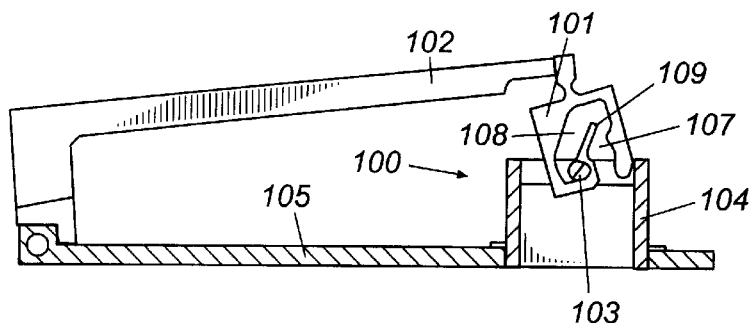
Figure 11D:
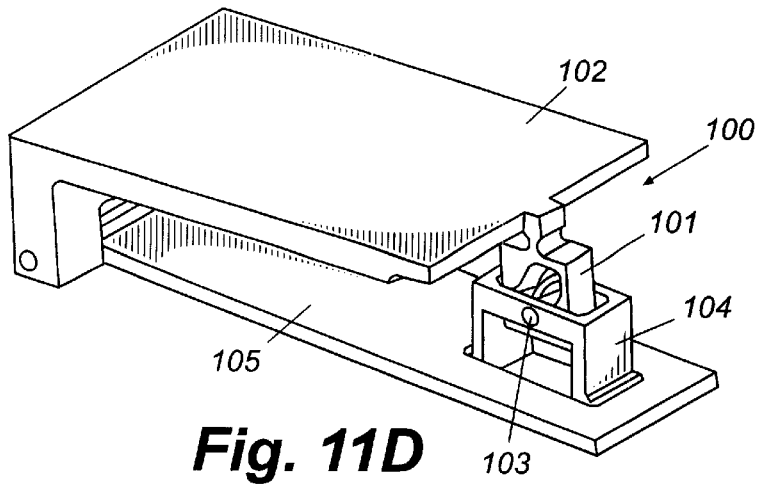
FIG. 11D is a perspective view of the locking mechanism as shown in FIG. 11A.

When the housing 102 is subsequently pulled away from the displaceable cover 105 (moving from FIG. 11B to FIG. 11C, the pin moves down inner slot 108, acting against the dividing member 109 to push the member 101 sideways. When the position shown in FIG. 11C is reached, the pin 103 locates a recess 110 (see FIG. 11B) in the lower end of inner slot 108, which allows the member 101 to relax slightly but still keeping a certain degree of stress on the member 101 by holding it away from the equilibrium position relative to the housing 102. In this way, the pin 103 latches into the recess 110 and locks the mechanism 100 permanently in the "post-use" configuration. In FIG. 11D, the mechanism 100 can be seen in the "pre-use" configuration, with the member 101, housing 102, pin 103, frame 104, and displaceable cover 105 visible.

Figure 12A:
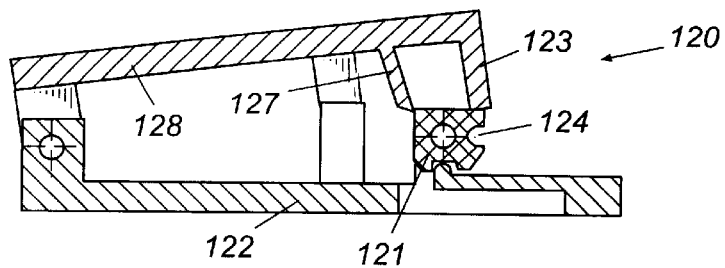
FIGS. 12A, 12B and 12C are schematic elevations of a third alternative embodiment of a locking mechanism, shown before, during and after use, respectively.
Figure 12B:
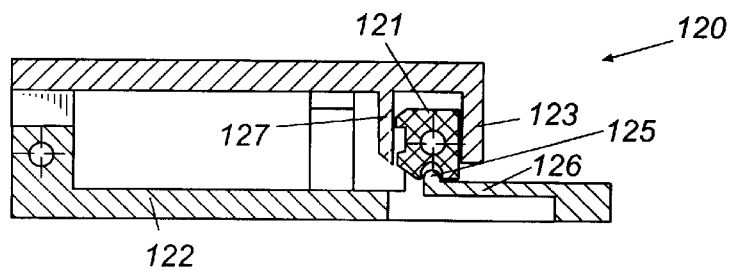
Figure 12C:
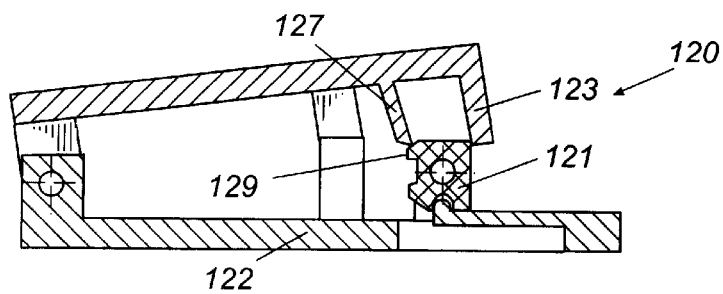
Figure 12D:
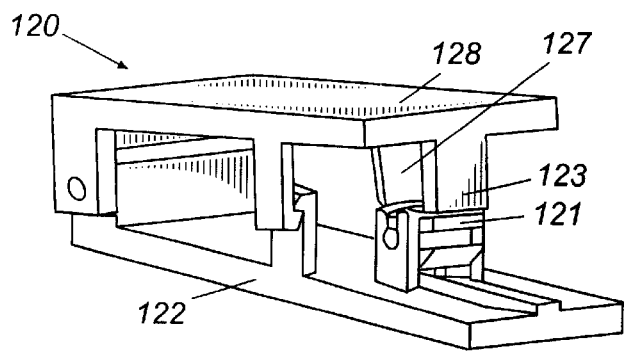
FIG. 12D is a perspective view of the locking mechanism as shown in FIG. 12A.

The third alternative embodiment of a locking mechanism of the present invention comprises generally a rotatable pawl assembly and is shown in FIGS. 12A–12D. The mechanism, indicated generally at 120, comprises a rotatable pawl 121 mounted on the displaceable cover 122 and which is rotated by an arm 123 in moving from the "pre-use" to "in-use" positions (FIGS. 12A and 12B, respectively). When the rotatable pawl 121 reaches the "in-use" position, a recess 124 (FIG. 12A) receives a projection 125 located on a resilient portion 126 of the displaceable cover 122, providing a degree of resistance to further movement.

In moving from the FIGS. 12A to 12B positions, the rotatable pawl 121 acts against a flexible strut 127 depending from the housing 128. When the rotatable pawl 121 is in the FIG. 12B position, further clockwise rotation of the pawl is prevented by the arm 123.

When the housing 128 is lifted (moving from FIGS. 12B to 12C), the strut 127 acts against a projection 129 urging the rotatable member 121 in a clockwise direction, but the arm 123 prevents such rotation. As the housing reaches the FIG. 12C position, the strut 127 springs past the projection 129 to sit in a recess above the projection 129, and the arm 123 clears the upper corner of the rotatable pawl 121. When in this configuration, the arm 123 prevents any counter-clockwise rotation of the rotatable pawl 121, while the strut 127 prevents any clockwise rotation thereby locking the rotatable pawl 121 in position and preventing any further downward movement of the housing 128 towards displaceable cover 122.

Figure 13C:
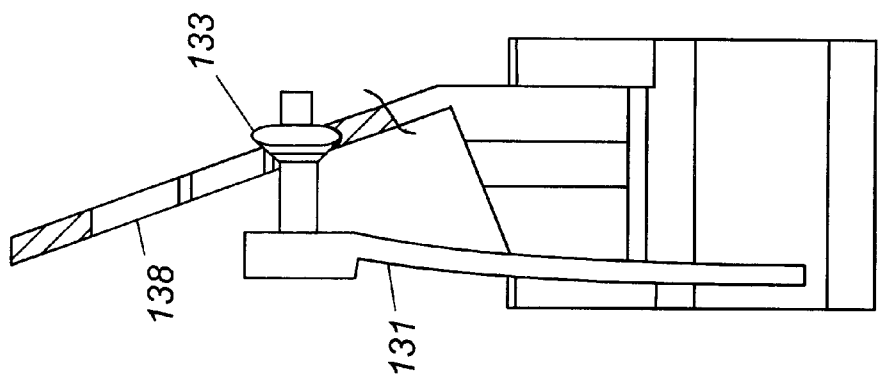
FIGS. 13A, 13B and 13C are schematic elevations of a fourth alternative embodiment of a locking mechanism, shown before, during and after use, respectively.
Figure 13B:
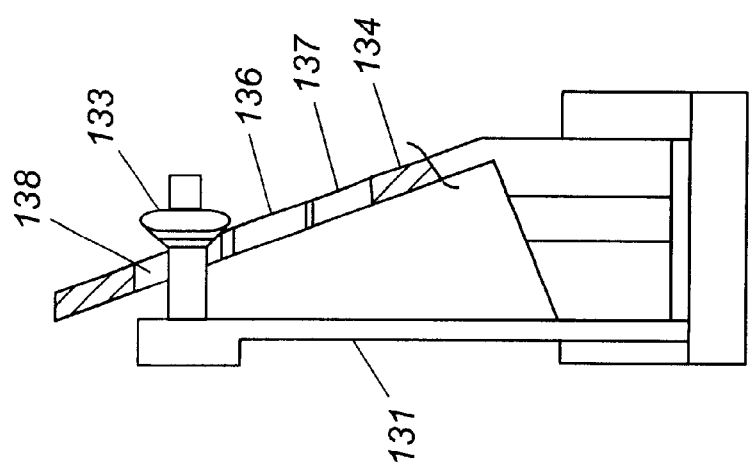
Figure 13A:
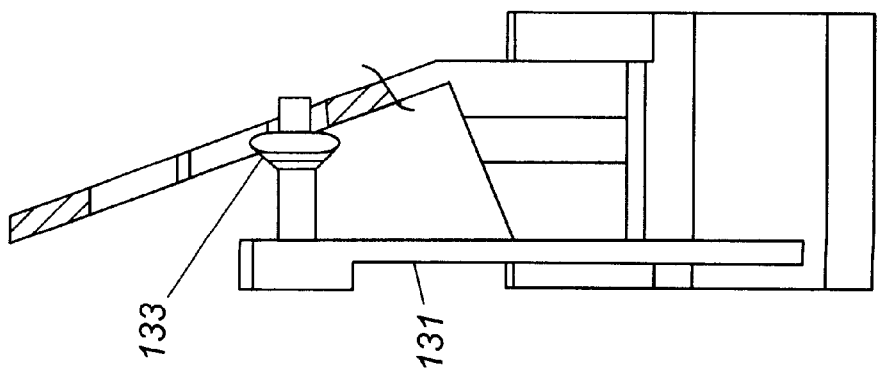
Figure 13D:
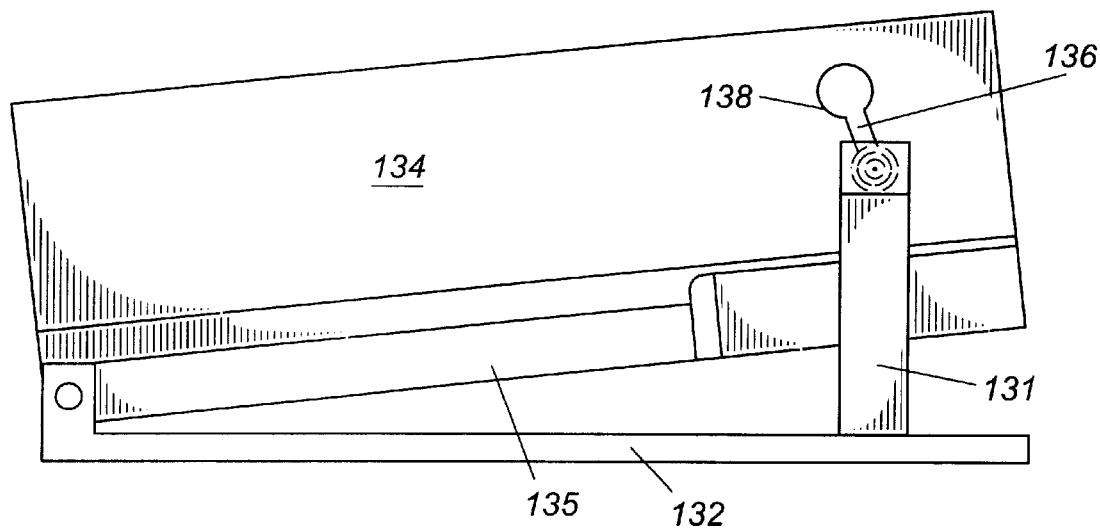
FIG. 13D is a side elevation of the locking mechanism as shown in FIG. 13A.
Figure 13E:
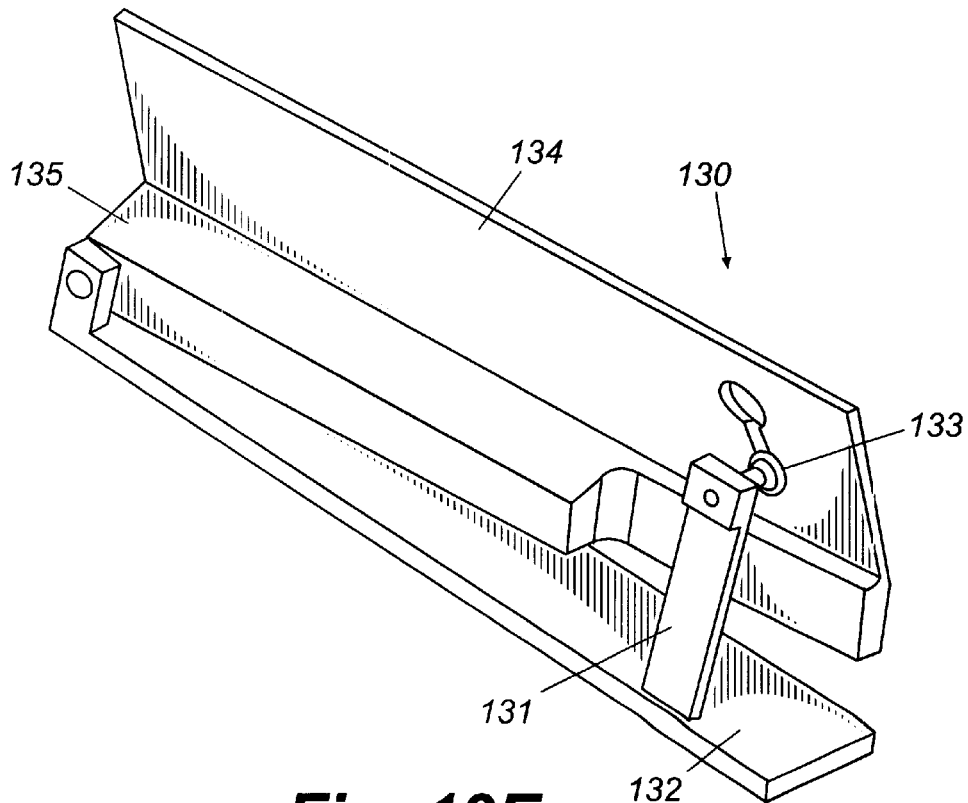
FIG. 13E is a perspective view of the locking mechanism as shown in FIG. 13A.

The fourth alternative embodiment of a locking mechanism of the present invention comprises generally a flexible post assembly as shown in FIGS. 13A–13E. In FIG. 13A the locking mechanism is indicated generally at 130 and comprises a vertical flexible post 131 (see FIGS. 13D and 13E) mounted on the displaceable cover 132 and having a projection 133 extending therefrom towards a sloped surface 134 on the housing 135.

A slot 136 in surface 134 connects two apertures, namely a lower aperture 137 (see FIG. 13B) which is of smaller diameter than the widest part of projection 133, and an upper aperture 138 which is of larger diameter than the widest part of projection 133.

In the "pre-use" position, projection 133 is positioned at the lower aperture. As the housing moves towards the "in-use" position (FIG. 13B) the flexible arm 131 is bent back until the projection 133 reaches the upper aperture 138 whereupon it springs back into position as the projection 133 moves through the upper aperture 138.

In moving to the "post-use" position, the projection 133 is constrained by the slot 136 and the arm 131 is bent forward until the projection 133 reaches the lower aperture 137 which provides a recess for the projection 133 to spring back into (but not through). Because the arm 131 remains bent forward slightly, this effectively traps the projection 133 in the lower aperture 137 and thereby holds the mechanism permanently in the "post-use" configuration, as shown in FIG. 13C.

Figure 14:
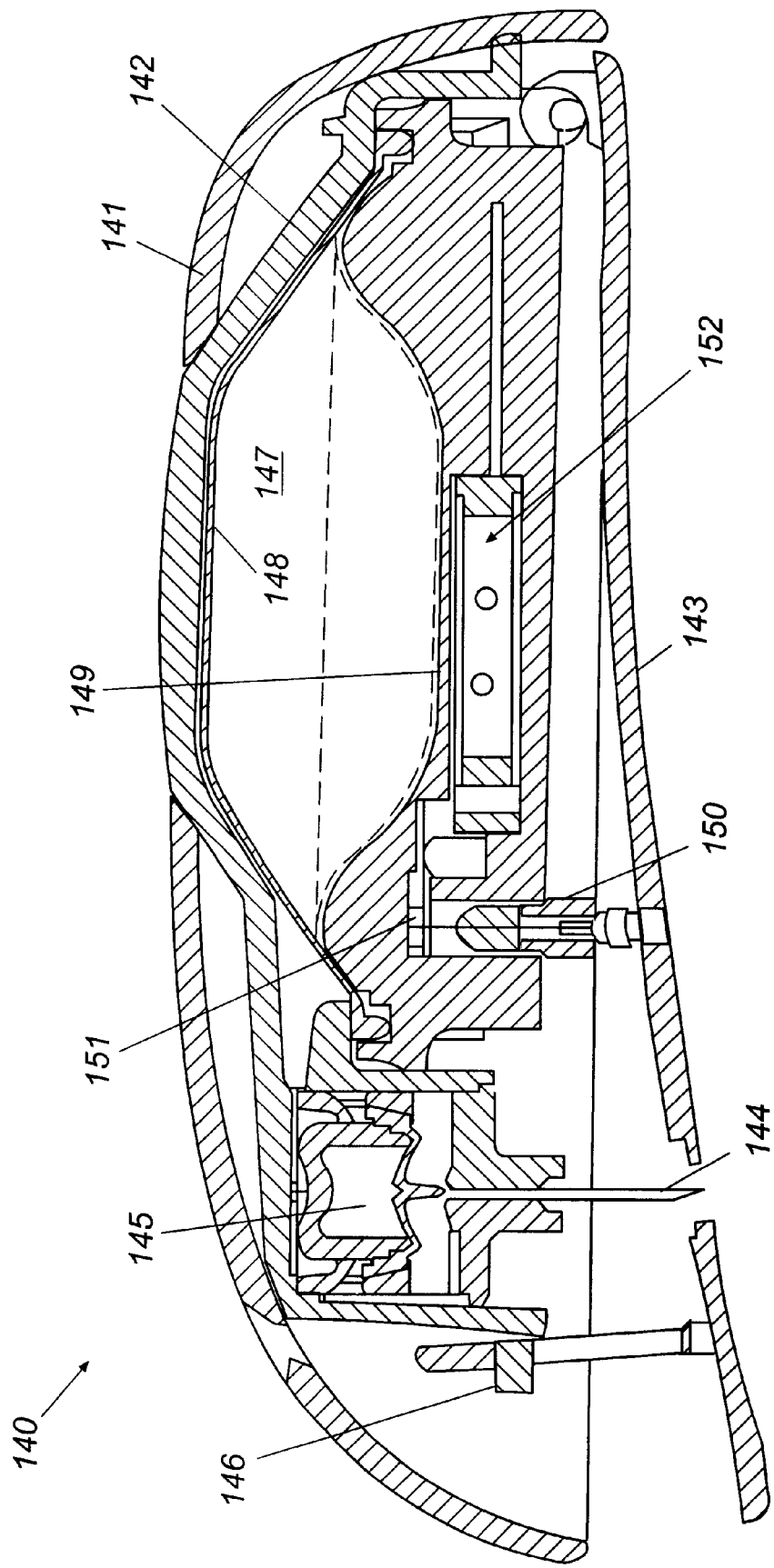
FIGS. 14 and 15 are sectional elevations of a third embodiment of drug delivery device according to the invention, shown before and during use, respectively.

In FIG. 14 there is another drug delivery device 140 according to the invention similar in many respects to the embodiments previously described. The device 140 has a protective upper cover 141, a housing 142, a displaceable cover 143, a delivery needle 144, a flow regulating chamber 145 and a three position locking mechanism 146.

The internal space of the drug delivery device 140 of FIG. 14 defines an expandable chamber 147 when the diaphragm 148 is in the position shown or a reservoir when the diaphragm is in the position shown in dotted outline at 149. The expandable chamber 147 is initially air filled (FIG. 14 shows the device in the pre-use configuration before medicament has been loaded). Thus, the reservoir is substantially of zero volume. The expandable chamber 147 communicates with the atmosphere via an open valve 150.

When liquid drug is loaded into the reservoir via a fill port (not shown), the diaphragm 148 moves downwards to position 149, with the reservoir filling with air and the expandable chamber 147 being emptied as the volume thereof decreases. Because the expandable chamber 147 is in communication with the atmosphere, the air initially filling the chamber 147 is exhausted into the atmosphere via the valve 150 without any necessity for action on the part of the user.

Furthermore, because the reservoir is initially of substantially zero volume, it does not require filling in any particular orientation. While prior art devices have required careful loading in order to ensure that all air bubbles are vented from the drug supply before delivery begins, the only air in the drug path of the device of FIG. 14 is in the short, narrow portion of the device between the reservoir and the needle 144. Thus, when drug enters the reservoir it immediately pushes the small amount of air ahead of it through the narrow space towards the needle 144, irrespective of the orientation of the device 140. By filling with the drug until a drop of the drug appears on the end of the needle 144 one can be sure that no air remains in the fluid path.

When the device 140 has been filled with drug, the diaphragm 148 is at the position shown at 149, and the valve 150 is open. However, when the displaceable cover 143 is applied to the skin, and the housing is pushed downwards, the valve 150 is closed and the closing of the valve actuates a switch 151 to begin generation of gas by an electrolytic cell 152 (described in more detail below).

Figure 15:
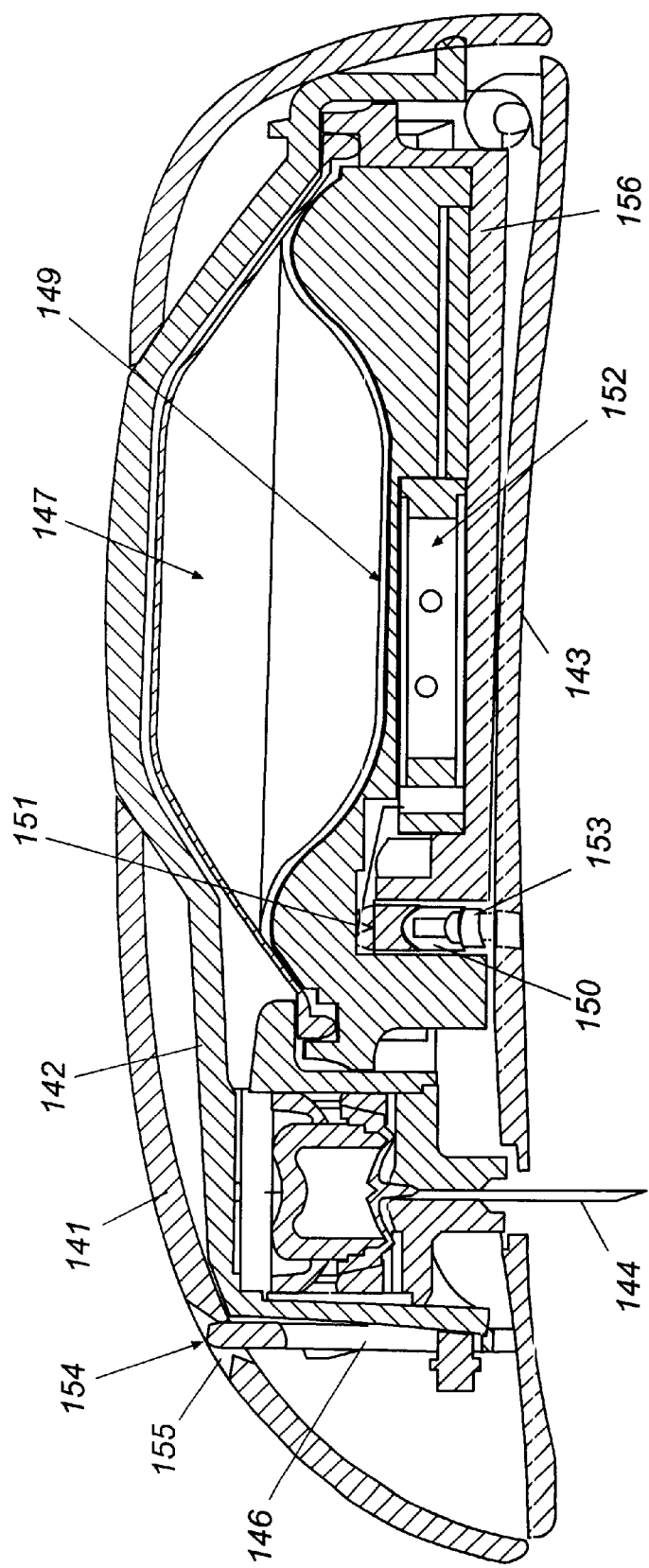

The device 140 is then in the "in-use" position shown in FIG. 15, with reservoir 147 filled with drug, the diaphragm 148 in position 149, valve 150 and switch 151 closed, and electrolytic cell 152 actuated to generate a gas and hence begin delivery of drug from reservoir to the patient through delivery needle 144.

Valve 150 is closed by a connecting member 153 which is connected to displaceable cover 143. When displaceable cover 154 moves towards housing 142, connecting member 153 fits into a valve 150 and pushes it home to seal the expandable chamber 147 (the area below diaphragm 149) from the atmosphere. When a gas is generated by the electrolytic cell 152, it pressurises the reservoir 147.

A coloured plastic member 154 forming part of locking mechanism 146 protrudes through an aperture 155 in the protective upper cover 141 when the device 140 is in the position as shown in FIG. 15. The coloured member 154 visually indicates that the device 140 has been actuated.

Figure 16:
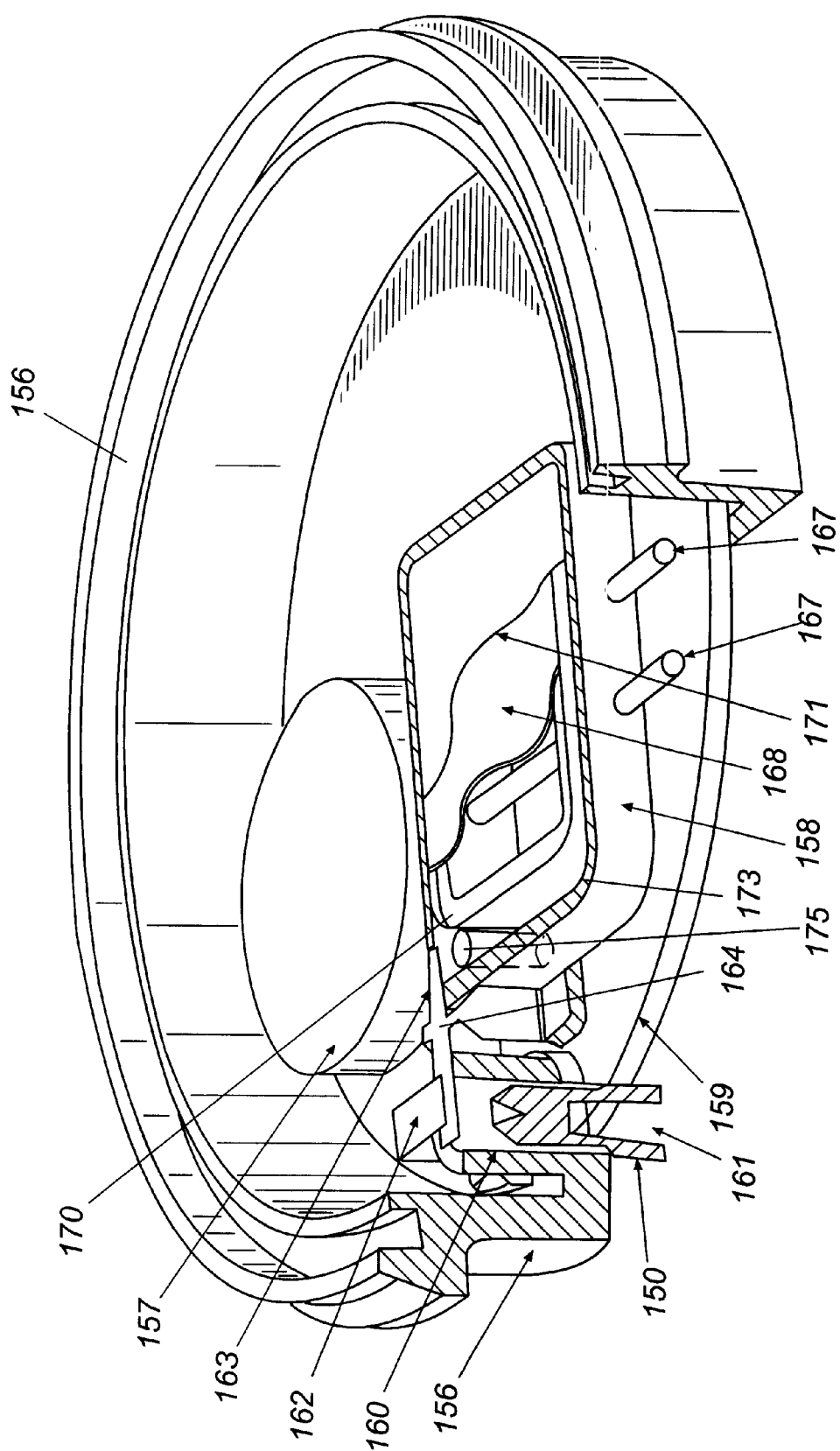
FIG. 16 is a partially cut away perspective view of the lower part of the housing on the device of FIGS. 14 and 15, including various components housed therein.

FIG. 16 is a detail view of the lower section 156 of the housing 142 (see FIG. 15). The lower section 156 houses a battery 157 and an electrolytic cell 158, both mounted on a printed circuit board (PCB) 159. The PCB 159 can be provided with controlling circuitry as required in order, for example, to vary the rate of delivery, stop delivery if the rate of gas generation is too high, or control the operation of the device 140 in any other way required. In the embodiment shown, the device 140 is a disposable single-rate device which does not require advanced controlling circuitry, but more sophisticated devices are of course within the scope of the invention.

A cylindrical outlet 160 is formed in section 156, and this provides a valve seat for the valve 150. When the valve 150 is pushed upwards into an outlet 160 it makes an airtight seal, as shown in FIG. 15. A recess 161 in the valve 150 tightly accommodates the connecting member 153 (FIG. 15), and the force used to push the housing 142 down onto displaceable cover 143 as described above is sufficient to jam the connecting member 153 into the valve 150. This design enables the device 140 to be removed from the skin by pulling housing 142 away from displaceable cover 143 to the "post-use" position, causing the connecting member 153 (which is permanently mounted on displaceable cover 143 and at this stage jammed into valve 150 also) to pull the valve 150 down and out of outlet 160 so as to open the valve. Using this design, if the reservoir 147 is not empty when the device 140 is removed, and if gas generation continues, then the gas will escape through outlet 160 rather than driving further drug through the needle 144.

As described above, when the valve 150 is closed, it actuates a switch 151 (see FIG. 15) which comprises a fixed contact 162 and a rocking contact 163. This completes a circuit to connect a battery 157 to an electrolytic cell 158. When the valve 150 is pulled downwards as the device 140 is removed from the skin, the switch 151 should automatically disconnect because of the resilience of rocking contact 163 which pivots about a fulcrum 164. Thus, the opening of the valve 150 is generally a redundant feature and is important as a safety feature if the switch 151 does not automatically disconnect (leading to an unwanted continuation of delivery or, if the reservoir 147 is already empty, to a build up of gas pressure inside the device 140).

Figure 17:
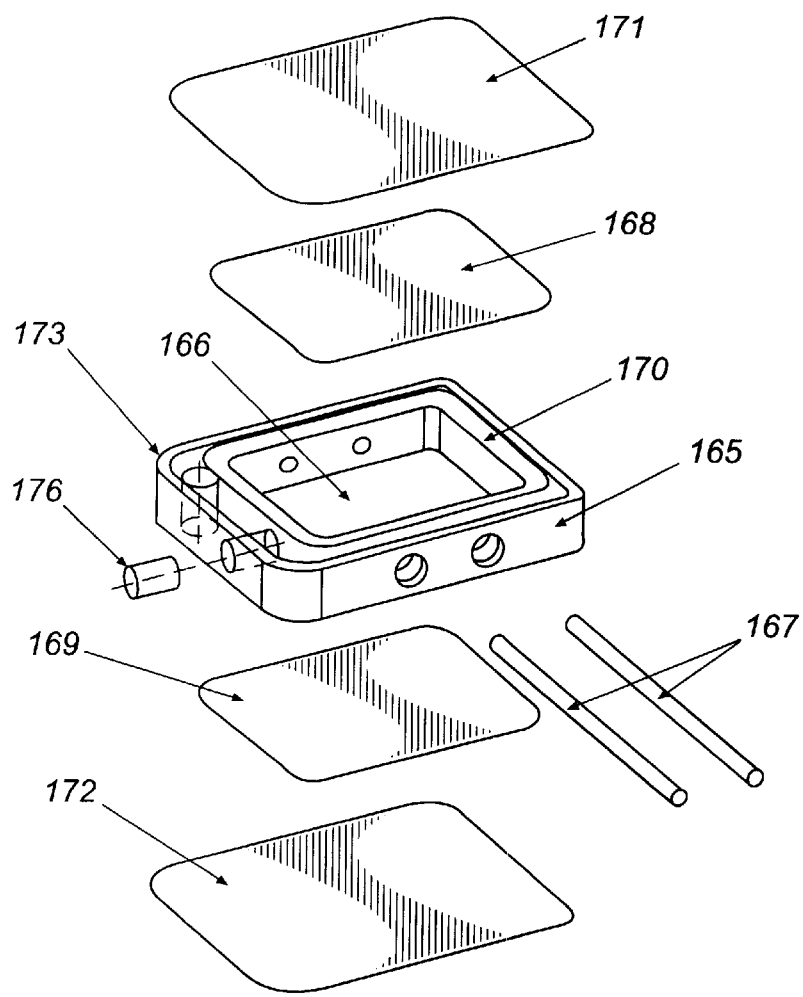
FIG. 17 is an exploded perspective view of the electrolytic cell used in the embodiment of FIGS. 14 and 15.
Figure 18:
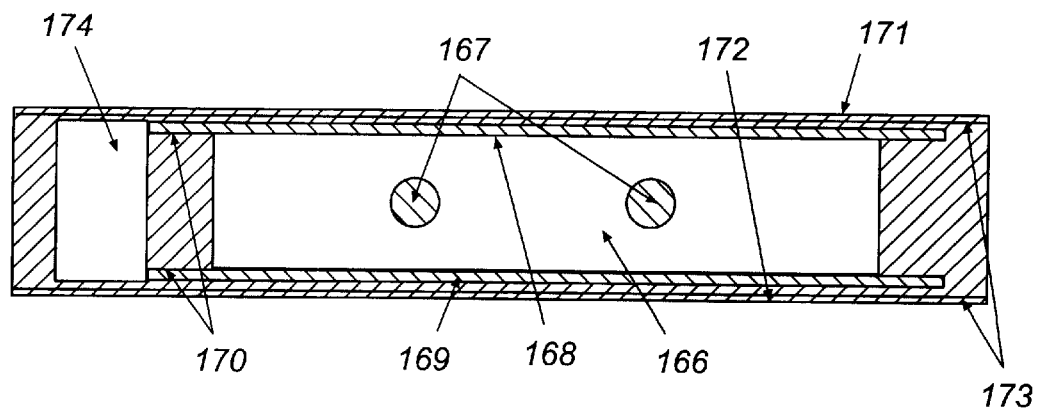
FIG. 18 is a sectional side view of the electrolytic cell used in the embodiment of FIGS. 14 and 15.

The electrolytic cell 158 comprises (see also FIGS. 17 and 18) a body 165 defining an internal space 166 for an electrolyte and through which a pair of electrodes 167 pass, each electrode being connected to a terminal of battery 157 (FIG. 16).

The internal space 166 is enclosed above and below by a pair of hydrophobic filters 168,169. These filters 168,169 retain the electrolyte but allow gas generated in the cell 158 to be released to the expandable chamber 147. The top and bottom of the body 165 is provided with a seating 170. The filters 168, 169 are placed in the seating 170 above and below the body 165 and are sealed in place.

The cell 158 is then sealed above and below by aluminium foil layers 171,172. A connecting cell 174 sealed at both ends by foil layers 171,172 enables gas passing through the hydrophobic filters 168,169 to be released, once the top foil layer 171 has been pierced. A gap adjacent to the seating 170,171 enables gas escaping through hydrophobic filters 168,169 to reach the connecting cell 174. The foil layer 171 is pierced by a spike 175 carried on rocking contact 164 (see FIG. 16). Thus, when the device 140 is actuated, the foil layer 171 is pierced to unseal the cell 158. A hydrophobic filter 176 (see FIG. 17) is also carried in the body 165 to enable the cell 158 to be filled with electrolyte by injection.

Figure 19:
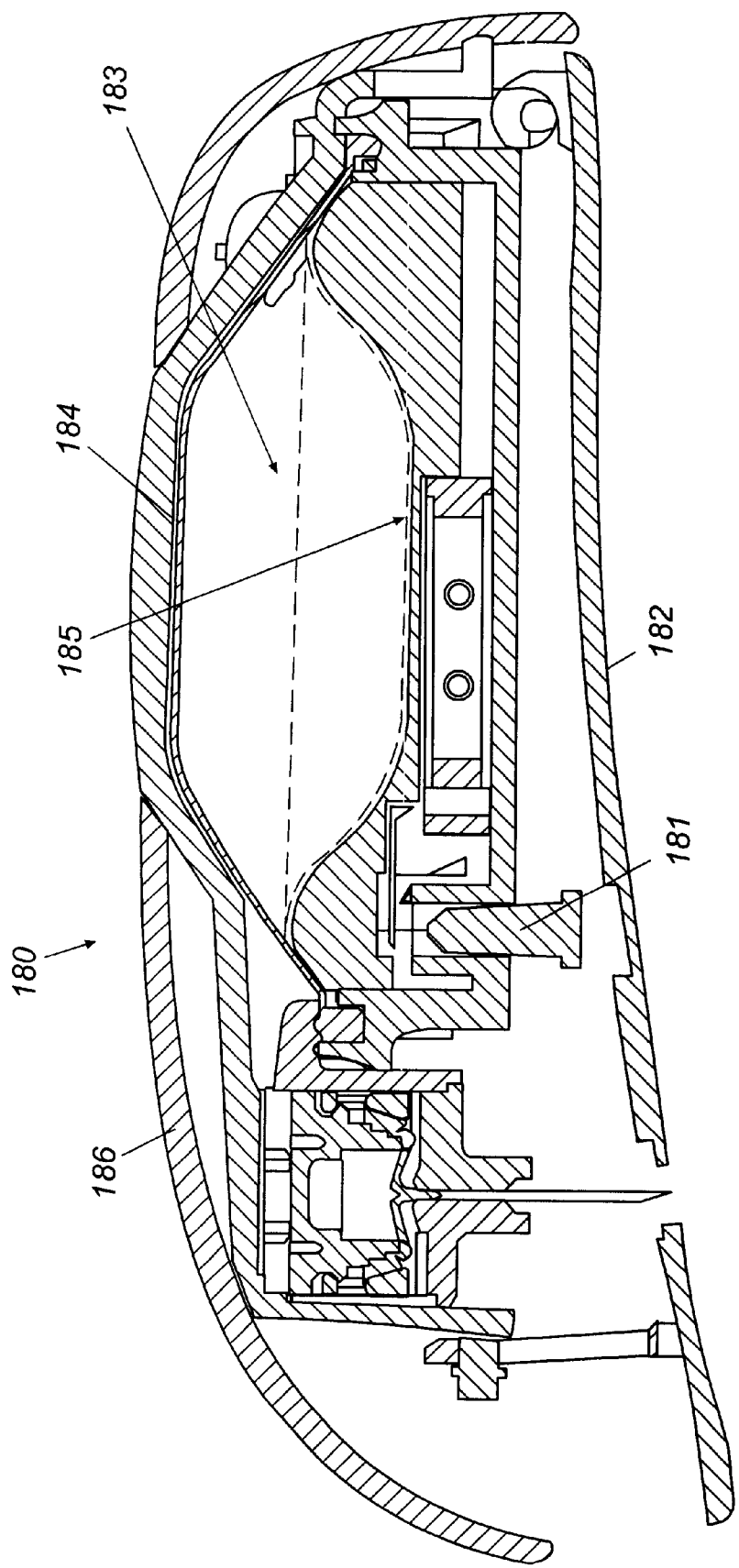
FIGS. 19 and 20 are sectional side views of a fourth embodiment of drug delivery device according to the invention, shown before and during use, respectively.
Figure 20:
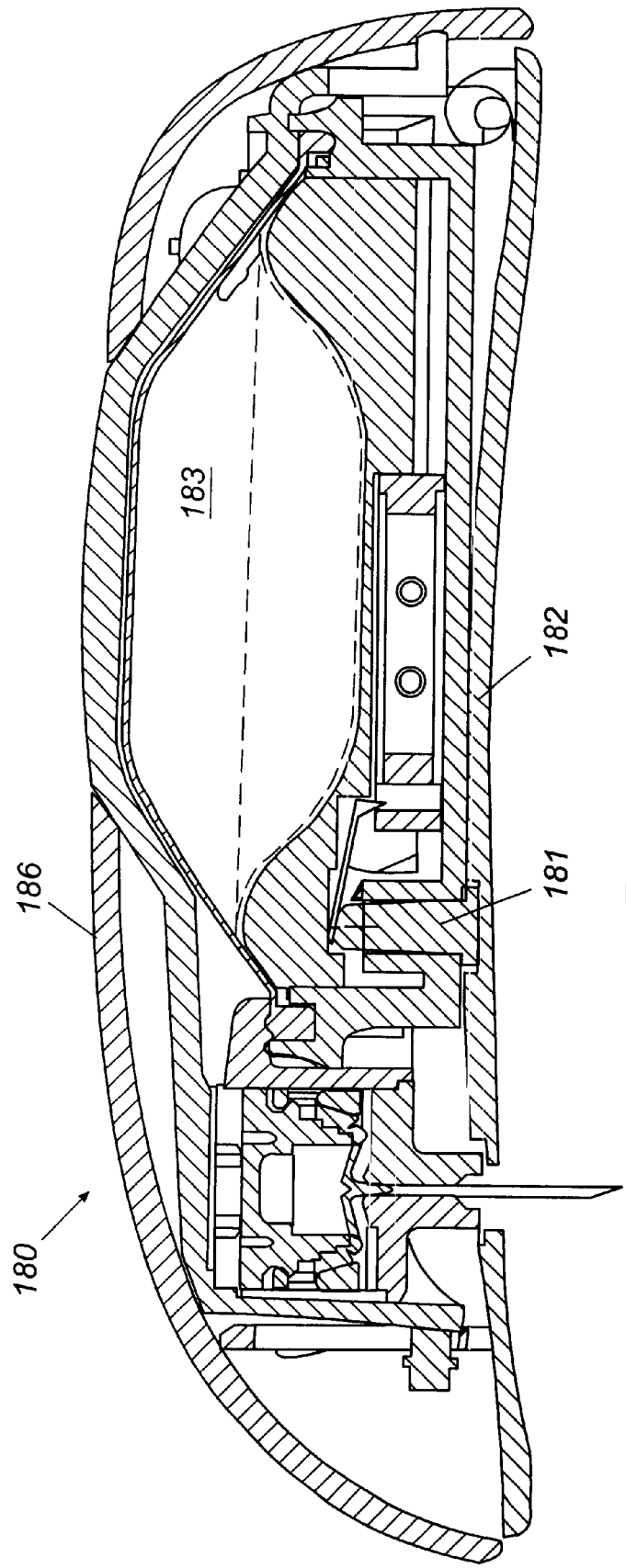

In FIGS. 19 and 20, a further embodiment 180 of the invention is shown. This embodiment differs from the embodiment of FIGS. 14–18 only in that the valve member 181 is not held by the displaceable cover 182 when the device 180 is removed from the skin after use. However, the valve 181 nevertheless achieves the primary purpose of allowing the internal space 183 to be occupied entirely by the expandable chamber when received by the user, with the diaphragm 184 moving to the position shown at 185 when the device 180 is loaded with medicament. This means that no air bubbles can be entrapped in the reservoir during filling, and the reservoir can thus be filled quickly and easily. The valve 181 closes automatically when the housing 186 is pressed towards the displaceable cover 182 (see FIG. 20).

Figure 21:
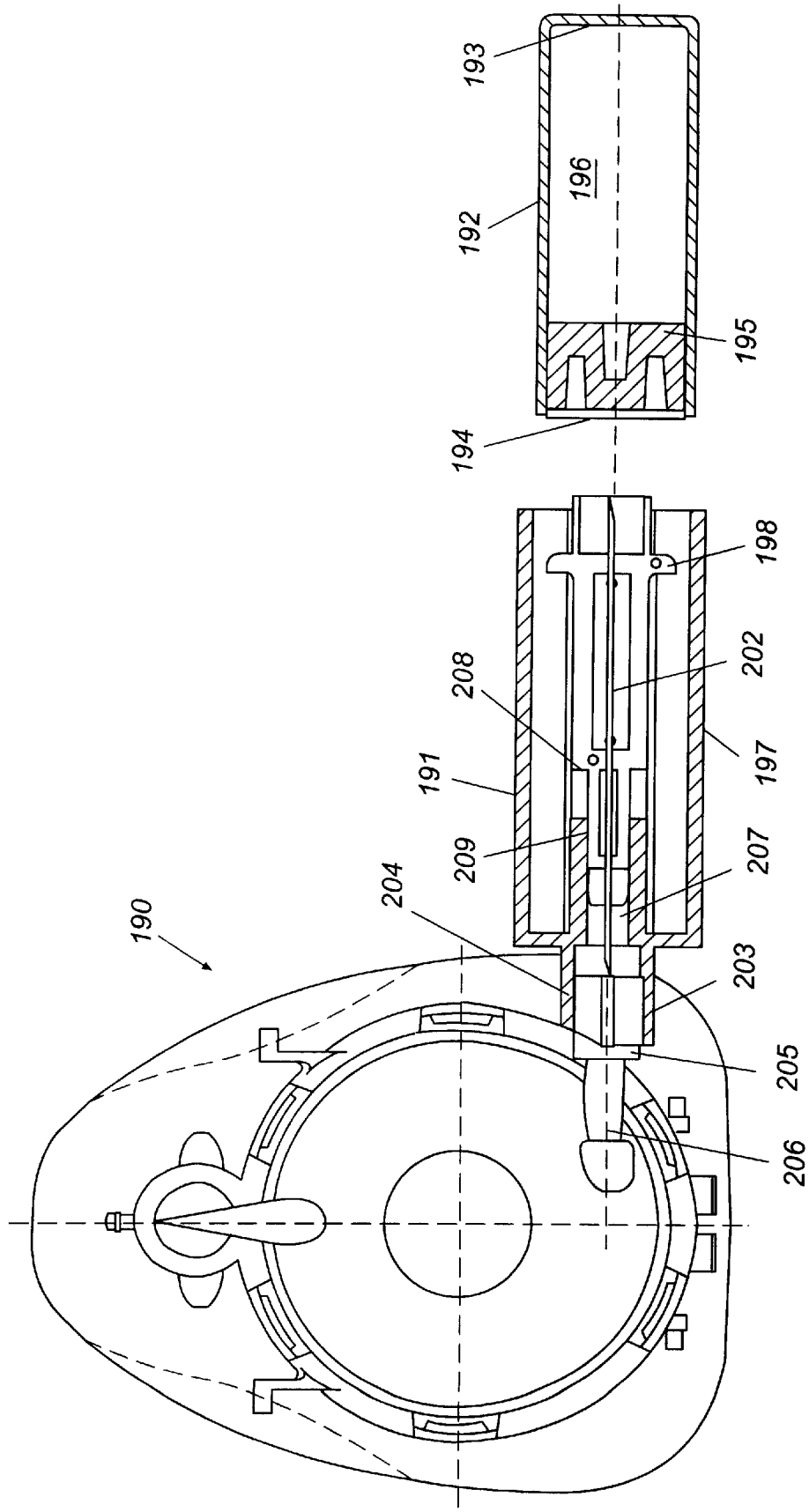
FIG. 21 is a sectional plan view of a drug delivery kit comprising the first embodiment of FIG. 1, a filling adapter and a medicament cartridge.

FIG. 21 shows a device 190 according to the invention which is identical to the device of FIG. 1, together with a filling adapter 191 and a drug-containing cartridge 192. Cartridge 192 is cylindrical in shape, closed at one end 193 thereof and sealed at the other end 194 by an elastomeric stopper 195 which is fittably mounted in the cartridge 192. Because the cartridge's liquid-filled internal space 196 is sealed, the stopper 195 is prevented by the incompressible nature of the liquid from moving in either direction.

Figure 22:
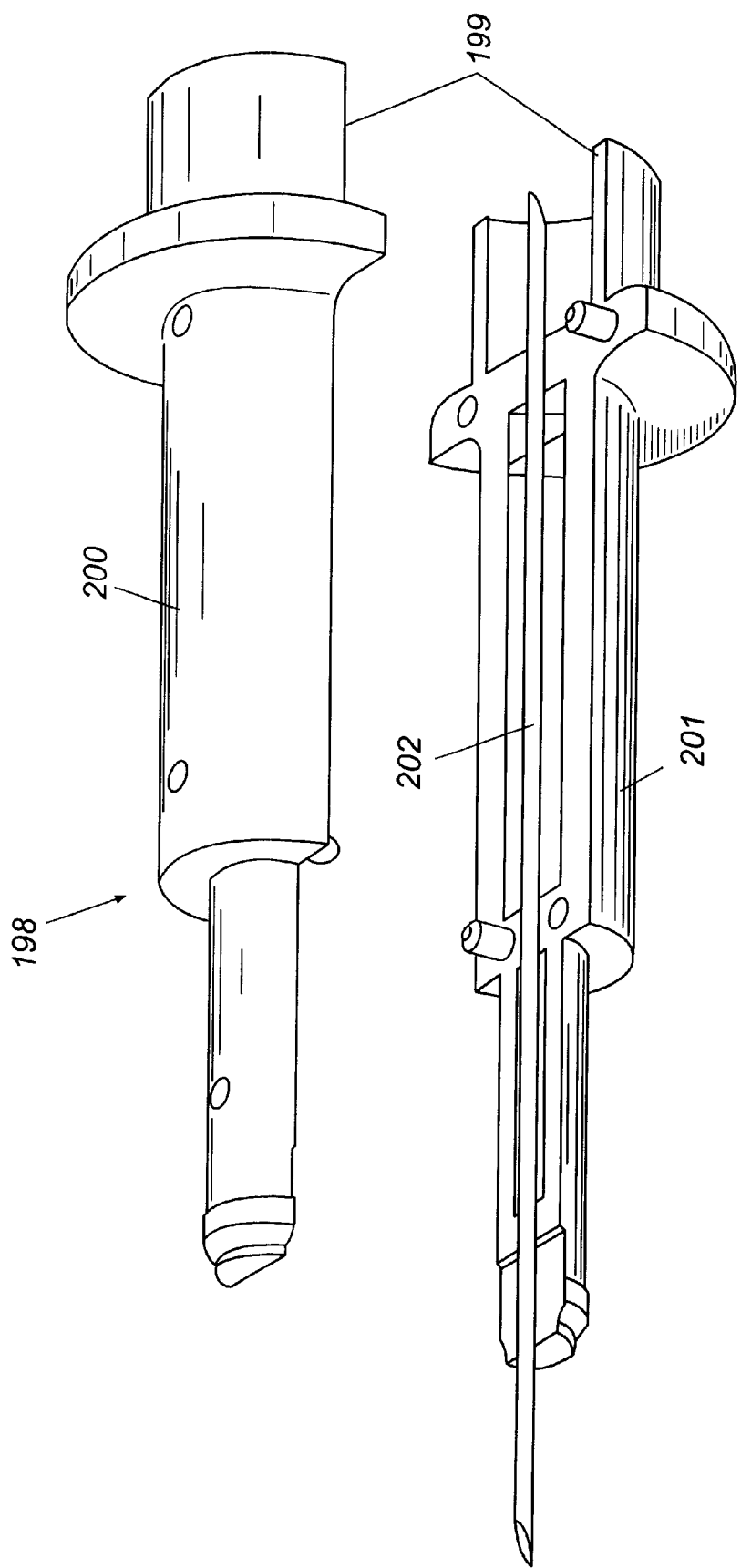
FIG. 22 is a perspective view of a subassembly used in the adapter shown in FIG. 21.

The adapter 191 has a housing 197 in which a cannula subassembly 198 is mounted. The subassembly 198 (see FIG. 22) includes a plastic body 199 moulded in two halves 200,201, which when assembled together clamp a double-ended hollow needle or cannula 202 in place.

A device 190 is provided with a socket 203 for receiving an adapter 191. A cylindrical projection 204 on the end of the adapter 191 is designed to fit into the socket 203, and also to conceal the cannula 202 to prevent injury before and after the adapter 191 is mounted on the device 190. A self-sealing penetrable plug 205 mounted in the socket 203 leads to a conduit 206 and an inlet for the reservoir (see inlet 19 in FIG. 1).

A subassembly 198 is mounted in a channel 207 of the adapter 191 such that it can be pushed inward until a shoulder 208 meets the end of the structure 209 defining the channel 207. At this point, the cannula 202 will penetrate the plug 205 enabling communication between the cannula 202 and the reservoir of device 190.

In use, a cartridge 192 is pushed into the adapter 191, whereby a stopper 195 causes the subassembly 198 to be pushed inwards and the cannula 202 to penetrate the plug 205. Since the subassembly 198 can move no further inward, further pushing of the cartridge 192 into the adapter 191 causes cannula 202 to penetrate stopper 195, thus putting drug-filled space 196 in indirect communication with the reservoir of device 190.

The stopper 195 is then held by subassembly 198, further pushing of the cartridge 192 inwards causes the stopper 195 (which remains stationary) to move relative to the cartridge 192 (which is progressively accommodated in the interior of adapter 191), with a consequent emptying of the contents of the cartridge 192 through the cannula 202 into the reservoir of device 190.

Figure 23:
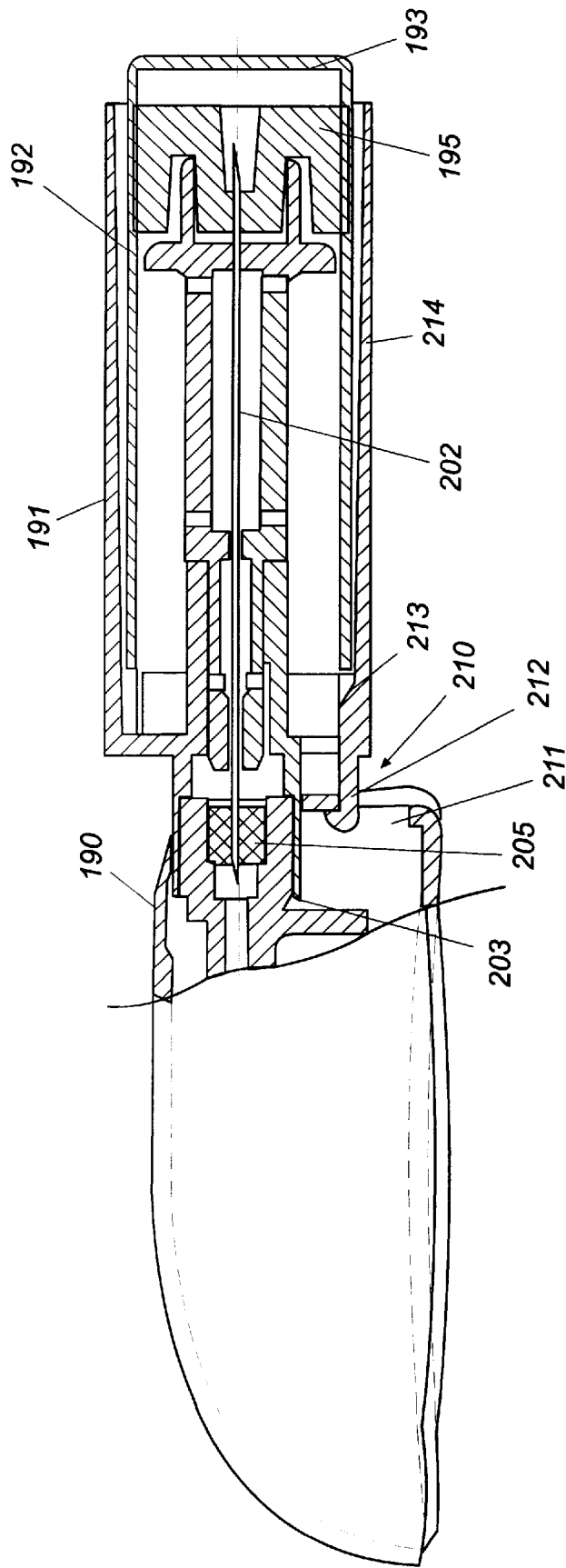
FIGS. 23 and 24 are sectional side views of the drug delivery kit of FIG. 21, shown during and after filling of the device, respectively.

This is illustrated best in FIG. 23, which shows a sectional view of the components shown in sectional plan view in FIG. 21, after the cartridge 192 has been pushed most of the way home into adapter 191. It can be seen that at this point, the stopper 195 (penetrated by cannula 202 which also penetrates plug 205) has almost reached the end 203 of cartridge 192.

The adapter 191 is not only held by the fit of the projection 204 into the socket 203, but also by a releasable locking mechanism 210. The releasable locking mechanism comprises an aperture 211 on the device 190 and a resilient catch 212 on the adapter 191 which is biased into the position shown in FIG. 23 so as to hold the adapter firmly in place on device. Preferably the adapter 191 and the device 190 are sold together in kit form, optionally with the adapter already mounted on the device.

When the cartridge 192 is pushed fully home it acts on a sloped section 213 of wall 214 of adapter 191 so as to push resilient catch 212, which is an extension of wall 214, downwards. This disengages the locking mechanism 210, allowing the adapter 191 to be removed from the device 190.

Figure 24:
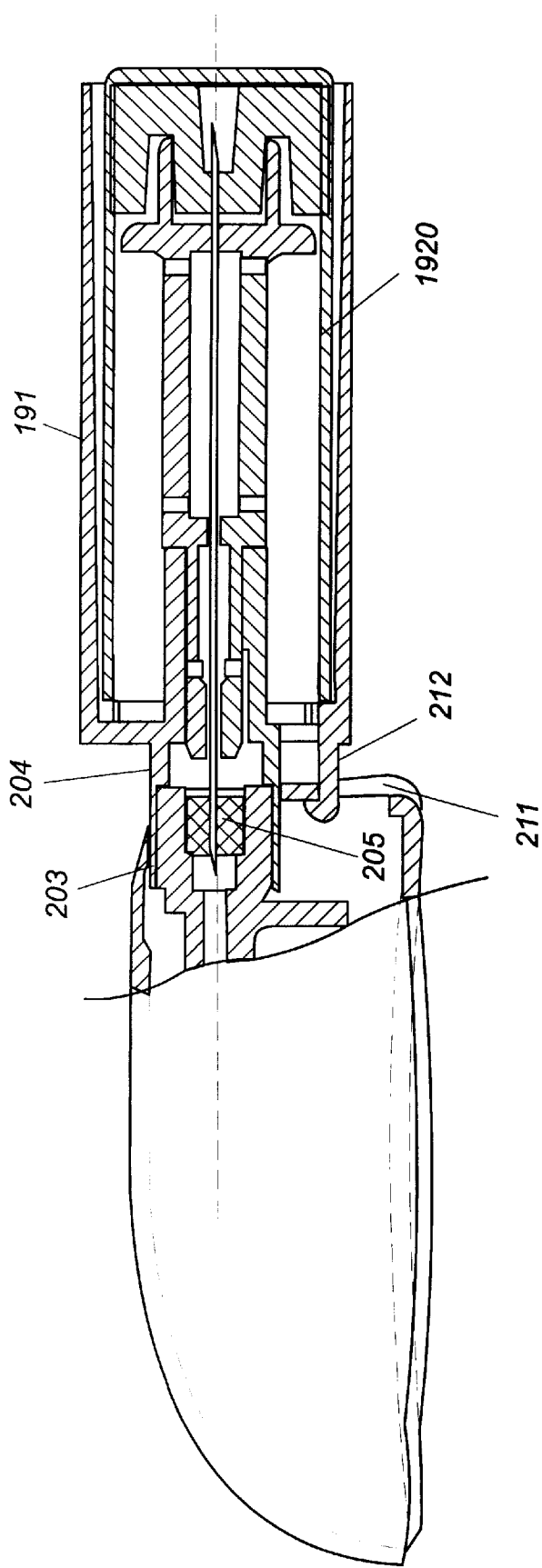

FIG. 24 shows the kit after the cartridge 192 has disengaged the catch 212 allowing it to be withdrawn from the aperture 211. This permits the adapter 191 to be removed from the device 190 by pulling the projection 204 from the socket 203 whereupon the plug 205 seals itself and thereby isolates the reservoir of the device.

Because the catch 212 is only disengaged when the cartridge 192 is fully emptied (i.e. when the stopper is pushed to the closed end 193 of the cartridge 192), one can ensure that the reservoir is loaded with exactly the correct amount of drug every time, thereby eliminating human error and making the kit more suitable for home administration.

Furthermore, because both ends of the cannula 202 at all times are concealed, the adapter 191 can be safely disposed of without risk of injury. The adapter 191 allows the drug to be transferred to the reservoir with sterility ensured, since the user does not at any time handle any of the components in the fluid path.

Figure 25:
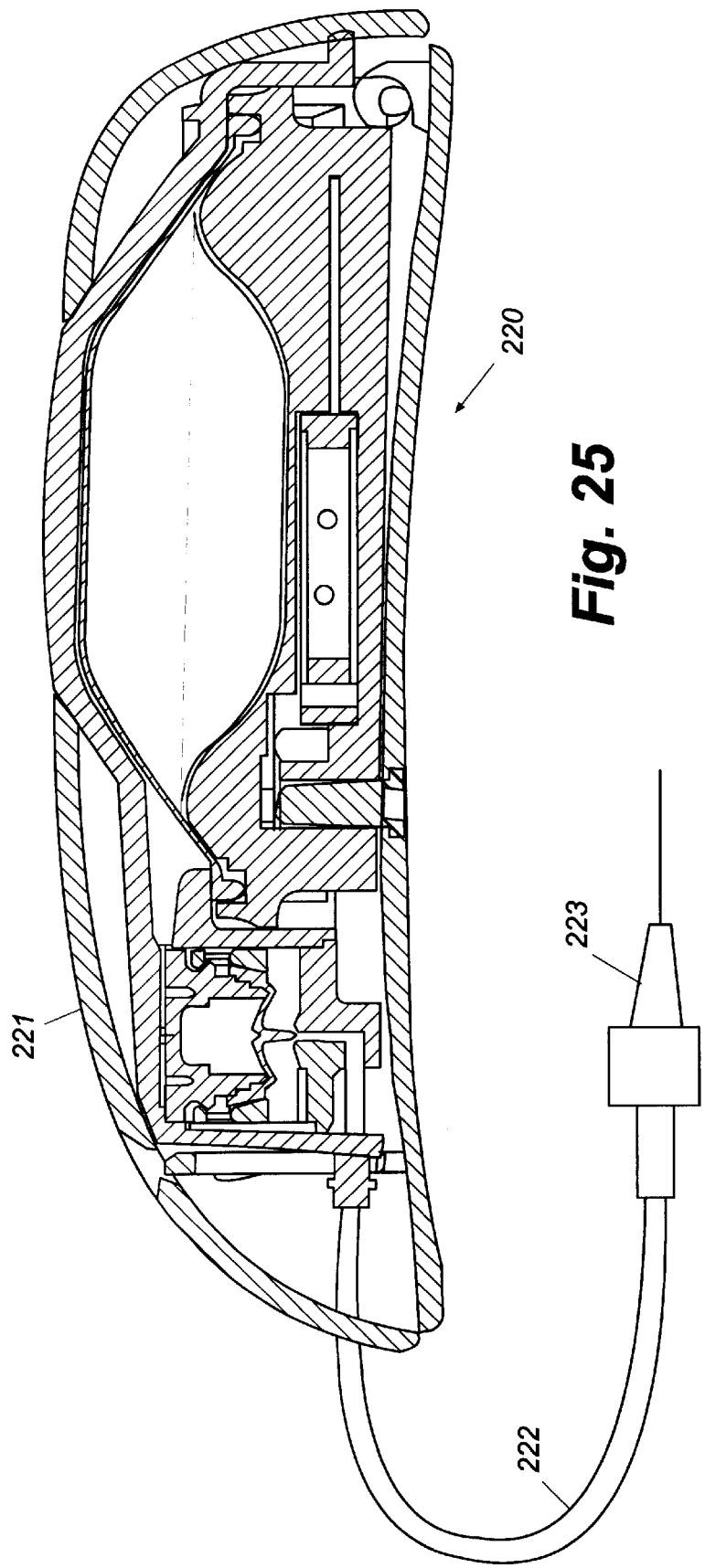
FIGS. 25 and 26 are sectional side views of fifth and sixth embodiments, respectively, of drug delivery device according to the invention.

FIG. 25 shows another alternative embodiment of the device according to the invention, indicated generally at 220. This embodiment differs from previous ones in that instead of a needle extending directly from the housing 221, a tube 222 extends from the housing 221 and carries a connector 223 thereon to which a needle may be affixed before use. This device 220 is particularly suitable for intravenous drug delivery because the tube 222 allows the needle to be accurately positioned in a vein.

Figure 26:
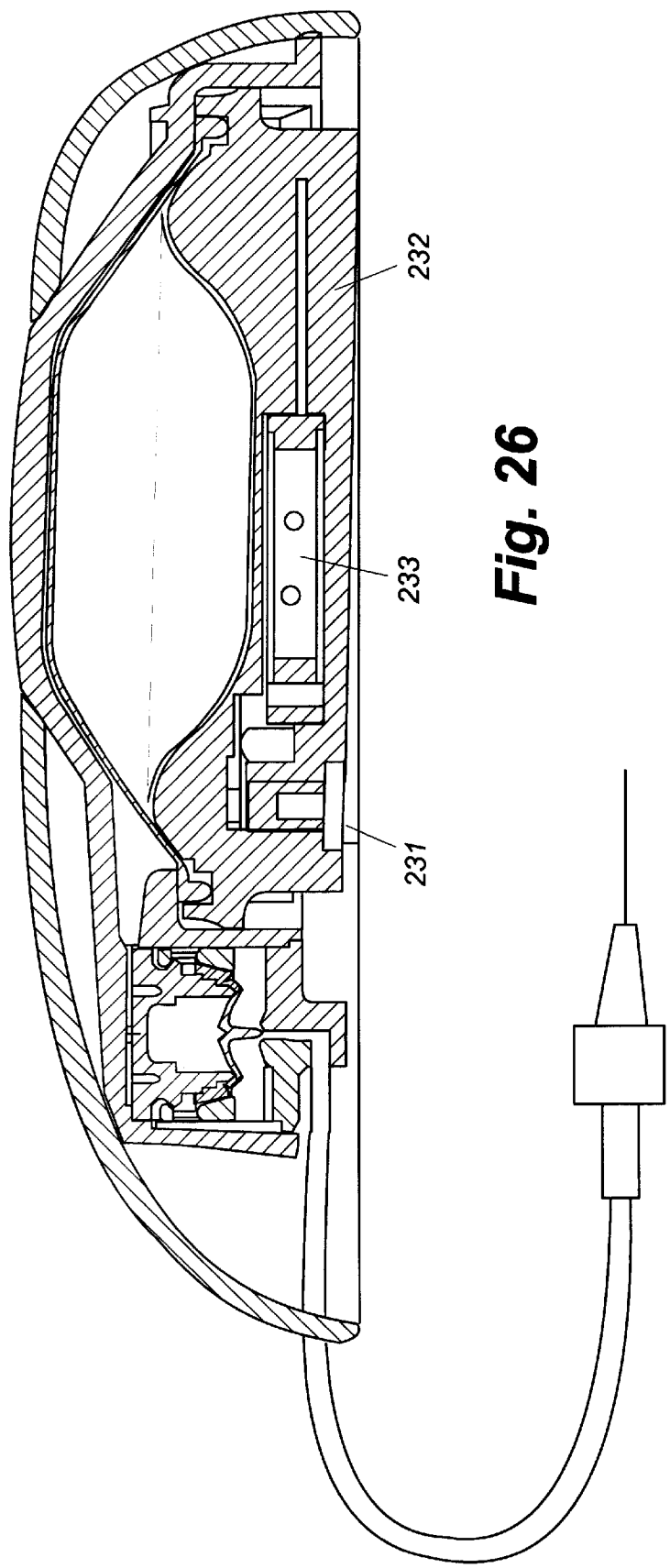

FIG. 26 shows an alternative intravenous embodiment, indicated generally at 230. In this embodiment the displaceable lower cover has been omitted and the device is actuated by a contact switch 231 positioned on the underside of the housing 232. When the device is applied to the skin, the switch 231 is pressed inwards (to the position shown in FIG. 26), thereby closing an electrical circuit and actuating a gas generating electrolytic cell 233 in the manner previously described. As the snap action provided by previously described devices is not required to cause a needle to penetrate the skin, the cover can be omitted without interfering with other functions of the device.

Figure 27:
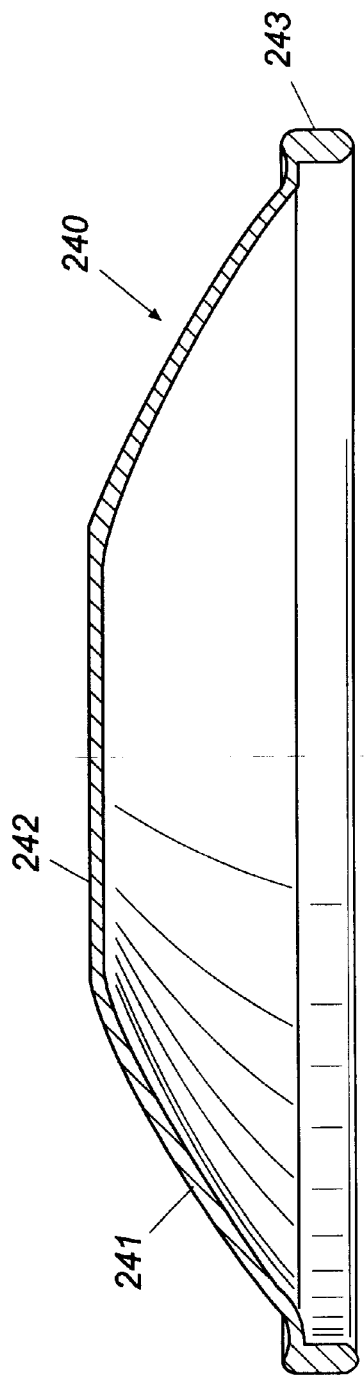
FIGS. 27 and 28 are sectional side views of a diaphragm suitable for use in a device according to the invention.

FIG. 27 shows the elastomeric diaphragm 240 utilised in the above-described devices according to the invention. The diaphragm 240 can also be used in other drug delivery devices according to the invention. The diaphragm 240 is shown in FIG. 27 in its relaxed position, as it would be when the reservoir is empty (see FIG. 6, for example). In this configuration the diaphragm 240 substantially has the form of a truncated cone having a sloped portion 241 surrounding a flat portion 242, with a lip 243 surrounding sloped portion 241 (lip 243 is used to attach diaphragm 240 to the housing of a drug delivery device).

Figure 28:
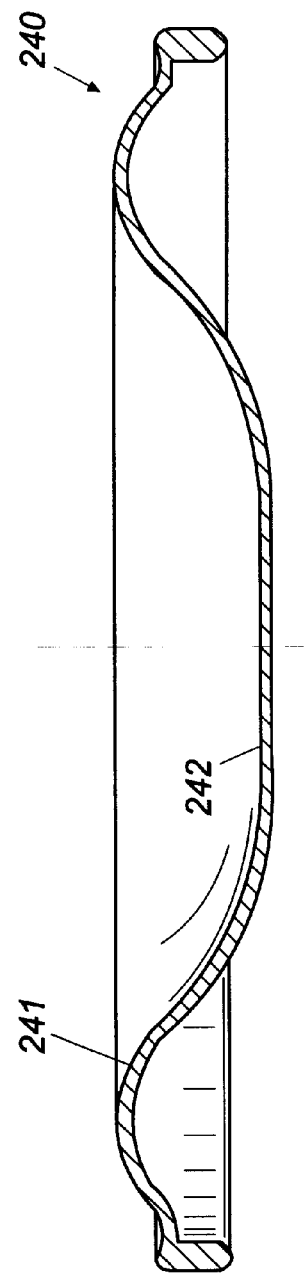

FIG. 28 shows the diaphragm 240 in the configuration in which the reservoir is full (see FIG. 1, for example). In this configuration, the central portion 242 is still flat, and the surrounding portion 241 has an arcuate curved cross-section, in the form of a substantially inverted U shape.

The diaphragm 240 is bistable, such that it is stable in either the FIG. 27 or the FIG. 28 configuration. However, a particular advantage has been found to result from the fact that in moving from the reservoir full (FIG. 28) configuration to the reservoir empty (FIG. 27) configuration, very little energy is needed.

Unlike many bistable arrangements, only minimal force is required to move between the stable configurations. In many bistable arrangements a substantial amount of energy is required to move from one configuration to a midpoint, at which the amount of stored energy is relatively high, following which the stored energy is released to complete the transition. The diaphragm 240, rather than flipping between configurations, makes a smooth transition. However, in contrast to a completely pliable body, which cannot be depended on to exert force uniformly, the diaphragm 240 will behave dependably since it is constrained in its movement between configurations. This means that a predictable manner of movement is combined with a minimal expenditure of energy in actually effecting the transition between bistable configurations.

The elastomeric diaphragm 240 (and others shown in alternative embodiments) and the flow diaphragm 26 of the flow regulating chamber 35 are elastomers. There are two preferred sources for this material. One is a bromobutyl compound made by Vernay Laboratories, Inc. of Yellow Springs, Ohio (material number: VL 911N7). The second is an ethyl propylene diene monomer ("EPDM") material number Bryant 850-55, made by Bryant Rubber.

There are several advantages in using these two materials. First, the material has a low durometer, which enables the material to remain soft. Moreover, it enables the diaphragm to keep air out and deflect from one stable position to the other with little energy. In addition, these elastomers provide a long shelf life. Another advantage is the ability to withstand gamma radiation without degradation of properties. As stated above, gamma radiation is used in some sterilisation procedures. The ability of these materials to withstand gamma radiation is very important as these materials will be assembled in the device and sterilised. An additional advantage of using these materials is their lack of toxicity.

Figure 29:
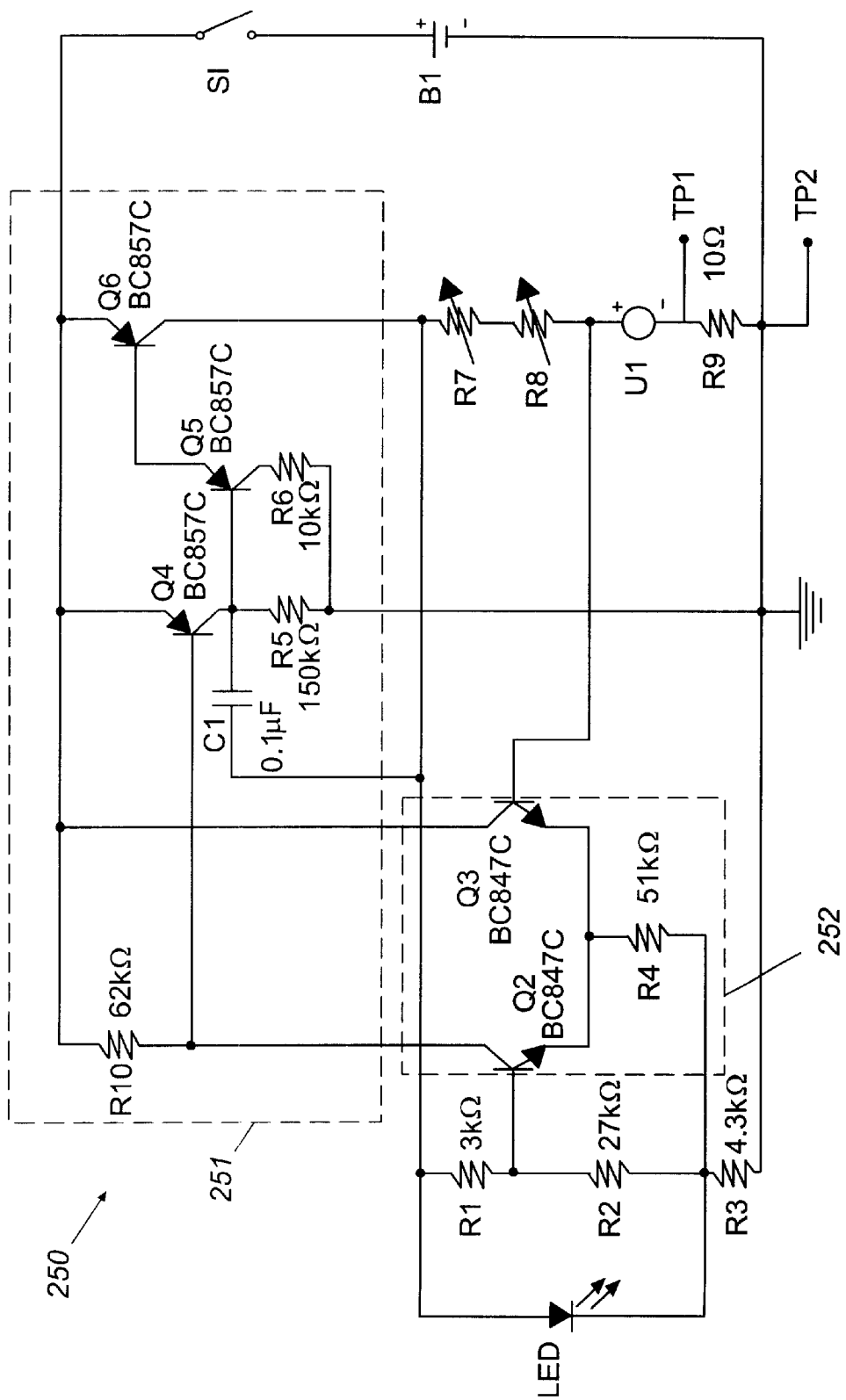
FIG. 29 is a diagram of an electronic controller circuit suitable for use in a device according to the invention.

FIG. 29 shows a circuit diagram of a controlling circuit particularly useful or a drug delivery device according to the invention. In the circuit 250, all symbols have their normal meanings within the art. The components shown are a battery B1, a switch S1 (activated by applying the device to the body), fixed resistors R1–R6 and R9–R10, variable resistors R7 and R8, a capacitor C1, transistors Q2–Q6, measurement terminals TP1 and TP2, a light emitting diode LED, and a load U1 which represents the electrolytic cell or other gas generating means. Reference numeral 251 denotes a section of the circuit 250 which functions as a current driver, and reference numeral 252 denotes a section of the circuit 250 which functions as an error circuit.

The current through the electrolytic cell U1 determines the potential drop across variable the resistance comprising resistors R7 and R8 (which may be adjusted to calibrate the device or set the delivery rate). This potential drop is compared by the error circuit with the potential drop across a reference resistor R1, which itself depends on the voltage drop across the LED. The value of resistor R1 is chosen to provide a potential drop equal to the drop measured across the resistors R7 and R8 when the correct current is flowing through the cell U1.

If the potential drop across the resistors R7 and R8 is lower than the constant potential measured across the resistor R1, indicating that the current through the cell U1 is too low (e.g. because of fading battery power, changes in the internal resistance of electrolytic cell U1 as the reactants are consumed, etc.), the error circuit 252 forces the driver 251 to increase the current flow to the correct value. In practice, the error circuit 252 continually ensures that the current does not deviate from the correct value by constant feedback operation.

Each of the transistors in the circuit 250 is a silicon-based bipolar transistor. The advantage of using bipolar transistors in particular is that they have been discovered to surprisingly withstand gamma radiation to a far greater extent than other types of transistors. The use of silicon as semiconductor is not essential but this material is currently less expensive than many other semiconductors. It has been found that by employing a circuit in which the or each transistor is a bipolar transistor, the circuit and hence the entire device can be subjected to intense gamma irradiation as a means of sterilising the device after manufacture. Conventional integrated circuits are destroyed by the intense radiation required to sterilise a device quickly.

For example, a dose of 2.5 Mrad (25 kJ/kg) of gamma radiation may be required to sterilise a device. In trying to design a circuit which would withstand such harsh conditions we consulted data regarding the electronic components used in space missions, such as the U.S. Space Shuttle missions. It was found that the same degree of radiation resistance was not required because the absorbed dose measured on the Space Shuttle averages approximately 0.4–0.5 Mrad.

As a rule, all electronic components will undergo a degree of degradation when subjected to irradiation. However, by selecting components which are resistant to irradiation as far as possible and whose performance can be predicted after receiving a given dose of radiation, it is possible to design a circuit which will withstand intense gamma radiation and still function in a predictable manner.

In particular, by using a bipolar transistor with a high current gain (e.g. a current gain of at least 600 but preferably 800 or more) the drop in current gain exhibited after irradiation can be compensated for in advance. This drop in gain can be of the order of a tenfold drop or more, but can be predicted well in advance. Furthermore, by using current values which are sufficiently low, the drop in voltage at the silicon junction of the transistor occurring as a result of the irradiation only slightly affects performance.

A further advantage is gained using a circuit which employs a light emitting diode as a basis for the reference voltage used in the error correction circuit, since the LED reference source is not affected by the gamma radiation. The LED used is a gallium arsenide (GaAs) based LED which has been found to provide particularly good resistance to gamma radiation.

In summary, the components and circuit employed have been found to be suitable for gamma irradiation, following which they give a well predictable performance in use. This enables the manufacture to be completed more efficiently, with the assembled device sterilisable by gamma radiation.

Figure 30:
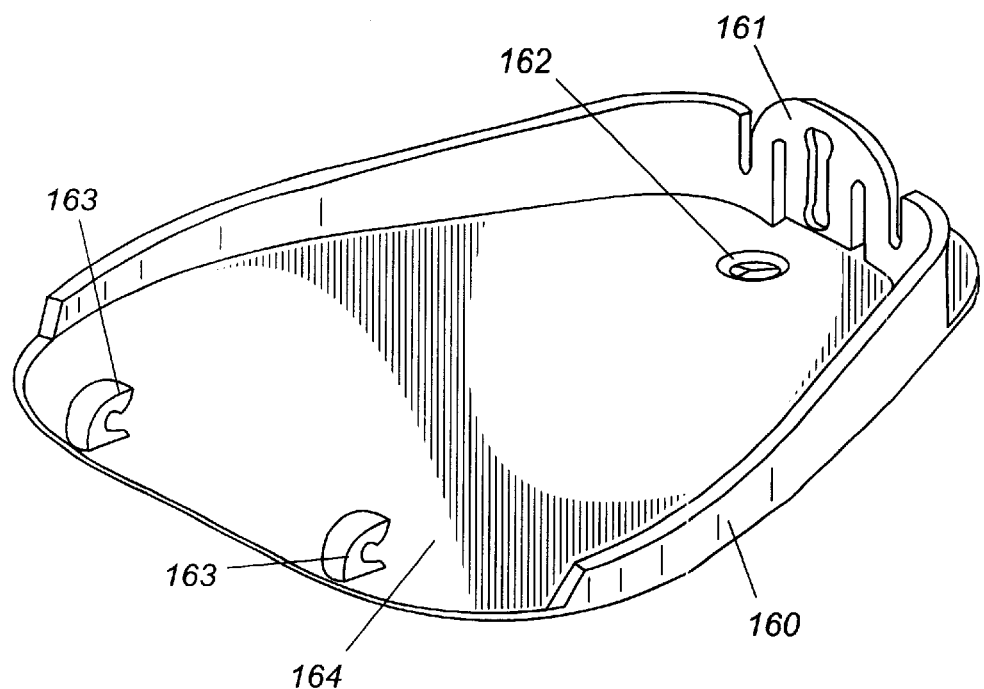
FIGS. 30 and 31 are perspective views of the top side and underside, respectively, of a displaceable cover from a device according to the invention.
Figure 31:
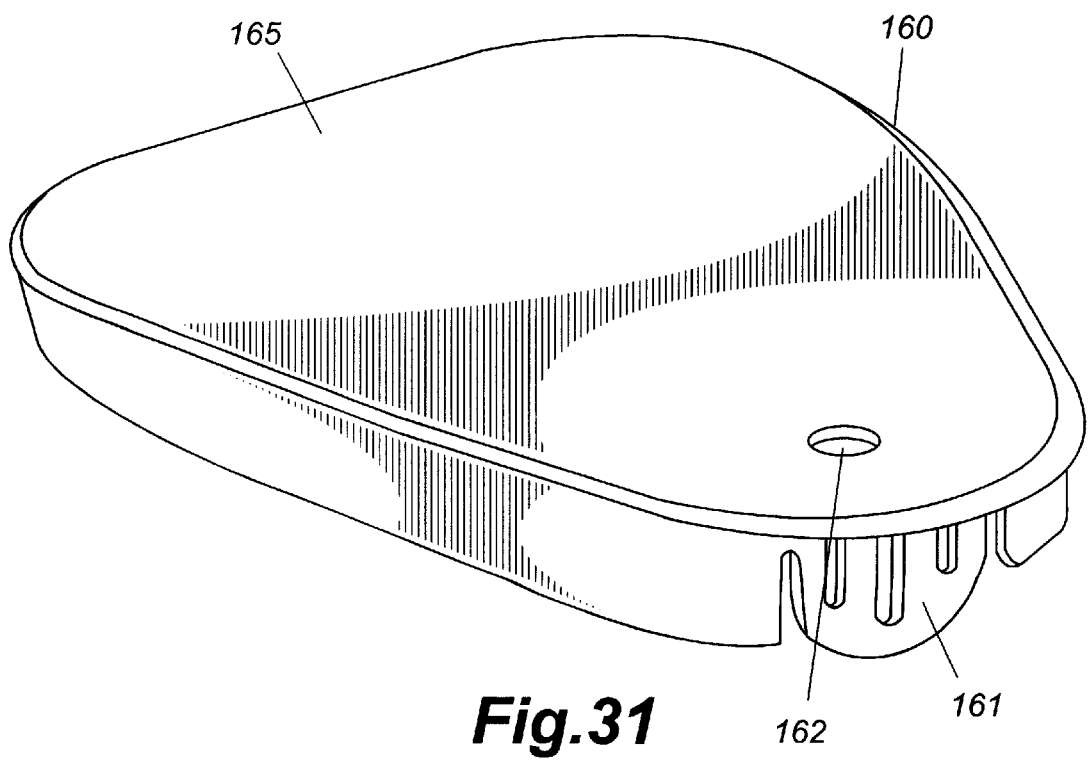

FIG. 30 is a perspective view of the top side of a displaceable cover 160 forming part of a device according to the invention. FIG. 31 is a perspective view of the underside of cover 160. Such a cover is described generally above in relation to the embodiment of FIGS. 4–8, for example.

The cover 160 is provided with formations 161 forming part of a locking mechanism as described above, with an aperture 162 through which a delivery needle protrudes in use. The cover 160 also has hinge formations 163 which enable the cover to be displaced relative to the housing between first and second positions as previously described.

The cover 160 is shaped to improve retention of the device against the skin: thus the top side 164 (FIG. 30) is convex, and the underside 165 (FIG. 31) from which the needle protrudes in use is concave. Accordingly, when the device has been applied to the skin of a subject removal of the device is resisted because the cover 160 conforms more closely to the skin. It is less likely that the device will peel from the skin without a conscious effort by the user since there is a lower likelihood of the periphery of the cover being detached from the skin.

It is further appreciated that the present invention may be used to deliver a number of drugs. The term "drug" used herein includes but is not limited to peptides or proteins (and memetics thereof), antigens, vaccines, hormones, analgesics, anti-migraine agents, anti-coagulant agents, medications directed to the treatment of diseases and conditions of the central nervous system, narcotic antagonists, immunosuppressants, agents used in the treatment of AIDS, chelating agents, anti-anginal agnets, chemotherapy agents, sedatives, anti-neoplastics, prostaglandins, antidiuretic agents and DNA or DNA/RNA molecules to support gene therapy.

Typical drugs include peptides, proteins or hormones (or any memetic or analogues of any thereof) such as insulin, calcitonin, calcitonin gene regulating protein, atrial natriuretic protein, colony stimulating factor, betaseron, erythropoietin (EPO), interferons such as $\alpha,\beta$ or $\gamma$ interferon, somatropin, somatotropin, somastostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues or antagonists thereof, such as IL-1ra, thereof; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and anlogues thereof; anti-emetic agents such as scopolamine, ondansetron, domperidone, metoclopramide, and analogues thereof; cardiovascular agents, anti-hypertensive agents and vasodilators such as diltiazem, clonidine, nifedipine, varapmil, isosorbide-5-mononitrate, organic nitrates, agents used in treatment of heart disorders, and analogues thereof; sedatives such as benzodiazepines, phenothiozines, and analogues thereof; chelating agents such as deferoxamine, and anlogues thereof; anti-diuretic agents such as desmopressin, vasopressin, and anlogues thereof; anti-anginal agents such as nitroglycerine, and analogues thereof; anti-neoplastics such as fluorouracil, bleomycin, and analogues thereof; prostaglandins and analogues thereof; and chemotherapy agents such as vincristine, and analogues thereof, treatments for attention deficit disorder, methylphenidate, fluoxamine, Bisolperol, tactolimuls, sacrolimus and cyclosporin.

It should be understood that the foregoing relates only to preferred embodiments of the present invention and that numerous modifications or alterations may be made therein without departing from the spirit and scope of the invention as set forth in the appended claims.

What is claimed is:

1. A subcutaneous drug delivery device comprising:

a housing having an internal reservoir and an expandable chamber disposed relative to the reservoir, a drug delivery needle extending from the housing for penetration of the skin of a subject, the needle having an outlet for drug delivery, a fluid path defined between the delivery needle outlet and the reservoir, means for providing a gas at a controllable rate into the expandable chamber, and a flow regulating chamber, in communication with the fluid path, which is capable of volumetric changes in response to temperature and/or pressure changes.

2. A device according to claim 1, wherein the flow regulating chamber is associated with a blocking member which moves within the fluid path upon expansion of the flow regulating chamber so as to restrict the flow of drug.

3. A device according to claim 2, wherein the blocking member comprises a formation provided on a displaceable member which at least partially bounds the flow regulating chamber, the formation being disposed adjacent to an inlet of a conduit forming part of the fluid path, such that restriction of the fluid path occurs when the blocking member is moved into the inlet of the conduit.

4. A device according to claim 2, wherein the blocking member is adapted to cut off the fluid path completely with a predetermined degree of expansion of the flow regulating chamber.

5. A device according to claim 1, wherein the expandable chamber causes contraction of the reservoir in use.

6. A device according to claim 1, wherein the flow regulating chamber alters the drug delivery rate by varying the flow resistance between the reservoir and the outlet.

7. A device according to claim 1, wherein a displaceable cover is connected to the housing such that displacement of the housing relative to the cover when the cover has been applied to the skin of a subject causes the delivery needle to penetrate the skin of the subject.

* * * * *